(12) United States Patent
Säll et al.

(10) Patent No.: US 10,524,873 B2
(45) Date of Patent: Jan. 7, 2020

(54) DEVICE FOR HANDLING MEDICAL WASTE PRODUCTS

(71) Applicant: Carebay Europe Ltd., Sliema (MT)

(72) Inventors: Daniel Säll, Segeltorp (SE); Stefan Gylleby, Stockholm (SE)

(73) Assignee: SHL Medical AG, Zug (CH)

( * ) Notice: Subject to any disclaimer, the term of this patent is extended or adjusted under 35 U.S.C. 154(b) by 172 days.

(21) Appl. No.: 15/564,129

(22) PCT Filed: Apr. 11, 2016

(86) PCT No.: PCT/EP2016/057897
§ 371 (c)(1),
(2) Date: Oct. 3, 2017

(87) PCT Pub. No.: WO2016/169799
PCT Pub. Date: Oct. 27, 2016

(65) Prior Publication Data
US 2018/0078326 A1 Mar. 22, 2018

(30) Foreign Application Priority Data
Apr. 20, 2015 (EP) .................................. 15164267

(51) Int. Cl.
*G08B 21/00* (2006.01)
*A61B 50/36* (2016.01)
(Continued)

(52) U.S. Cl.
CPC ............ *A61B 50/362* (2016.02); *A61B 50/36* (2016.02); *A61M 5/3205* (2013.01); *B65D 43/02* (2013.01);
(Continued)

(58) Field of Classification Search
CPC .............. A61B 50/362; A61B 19/0287; A61B 19/0288; B65D 83/10
(Continued)

(56) References Cited

U.S. PATENT DOCUMENTS

| 4,905,916 A | 3/1990 | Sorwick et al. |
| 5,193,678 A | 3/1993 | Janocik et al. |
| 5,918,739 A * | 7/1999 | Bilof ..................... A61B 50/362 206/366 |
| 5,947,285 A * | 9/1999 | Gaba ........................ B65F 1/10 206/366 |

(Continued)

FOREIGN PATENT DOCUMENTS

| GB | 2513108 A | 10/2014 |
| WO | 2008060474 A2 | 5/2008 |
| WO | 2014/204958 A1 | 12/2014 |

*Primary Examiner* — Tai T Nguyen
(74) *Attorney, Agent, or Firm* — McDonnell Boehnen Hulbert & Berghoff LLP

(57) ABSTRACT

The present invention relates to a device for receiving and handling specific medical waste products to be stored in a safe container (10; 100), comprising a receiving mechanism (14; 126) arranged with a compartment (48; 131) for receiving a medicament container, which compartment (48; 131) is operably arranged to be moved from a first position wherein a medical waste product may be entered into said compartment to a second position wherein the medical waste product is entered into the safe container (10; 100), at least one first locking element (25; 118) operably arranged to releasably lock said compartment (48; 131) from being moved to said second position, said at least one first locking element (25; 118) being configured such that a medical waste product placed in said compartment (48; 131) constitutes a keying element for unlocking said compartment (48), and a monitoring unit (60; 200) comprising a detection mechanism (64; 150, 170) capable of detecting that said compartment (48; 131) has been moved from said first position to said second position.

19 Claims, 29 Drawing Sheets

(51) Int. Cl.
    *A61M 5/32*     (2006.01)
    *B65D 43/02*     (2006.01)
    *G08B 7/06*     (2006.01)
    *A61B 50/00*     (2016.01)
    *A61B 90/00*     (2016.01)

(52) U.S. Cl.
    CPC ........ *G08B 7/06* (2013.01); *A61B 2050/0059* (2016.02); *A61B 2090/0803* (2016.02)

(58) Field of Classification Search
    USPC ........................ 340/540, 541; 588/249.5, 900
    See application file for complete search history.

(56) References Cited

U.S. PATENT DOCUMENTS

| | | | | |
|---|---|---|---|---|
| 5,972,291 | A * | 10/1999 | Healy | A61L 11/00 |
| | | | | 422/122 |
| 6,283,909 | B1 * | 9/2001 | Sharp | A61B 50/362 |
| | | | | 206/366 |
| 6,585,114 | B2 * | 7/2003 | Kennedy | A61M 5/3205 |
| | | | | 206/366 |
| 2007/0027432 | A1 * | 2/2007 | Radford | B08B 9/00 |
| | | | | 604/317 |
| 2008/0156818 | A1 * | 7/2008 | Panek | B65F 1/1468 |
| | | | | 220/737 |
| 2011/0259467 | A1 | 10/2011 | Maness | |
| 2011/0260878 | A1 * | 10/2011 | Rigling | G01G 19/52 |
| | | | | 340/665 |

* cited by examiner

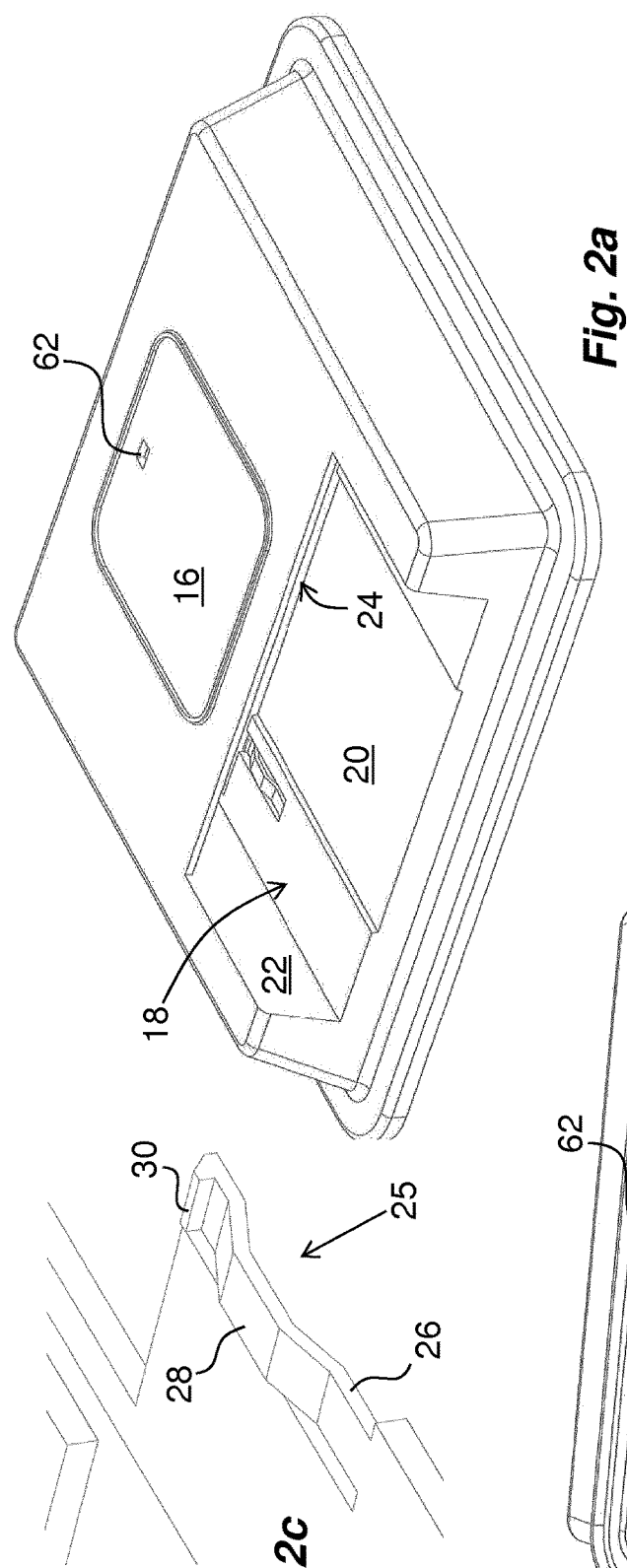
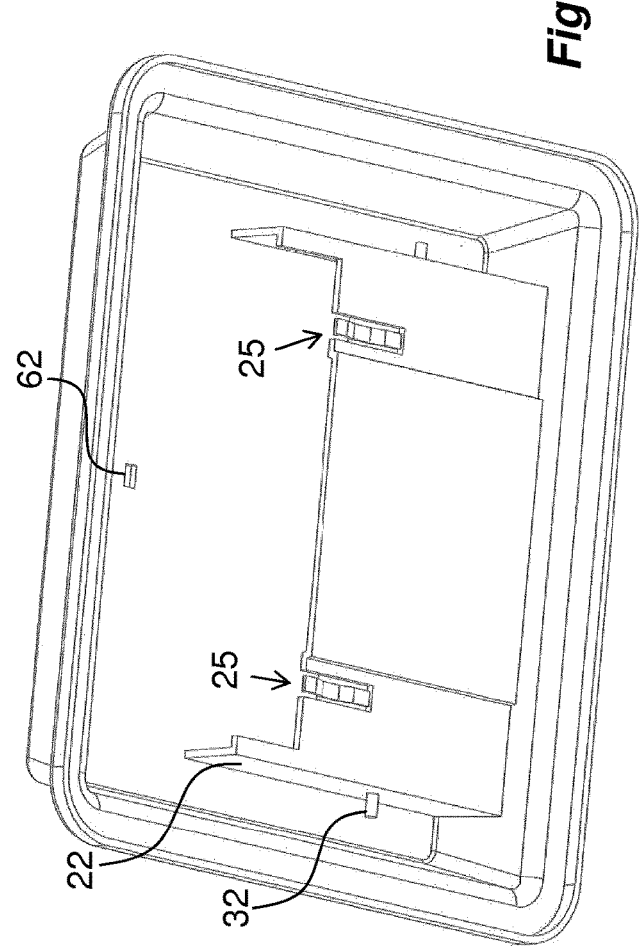
Fig. 2a
Fig. 2b
Fig. 2c

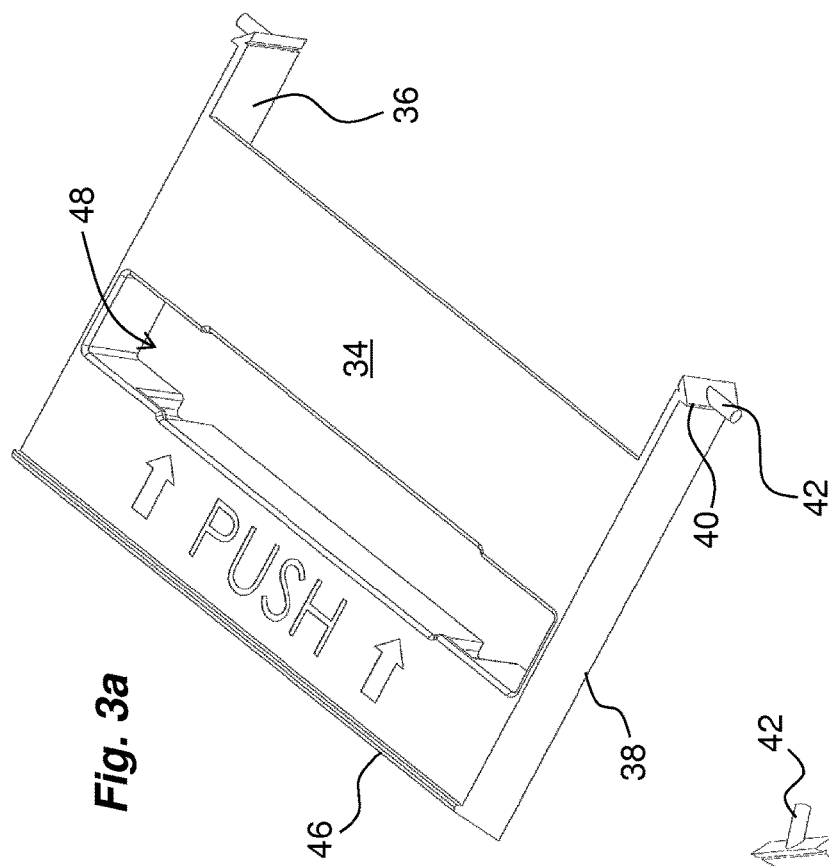
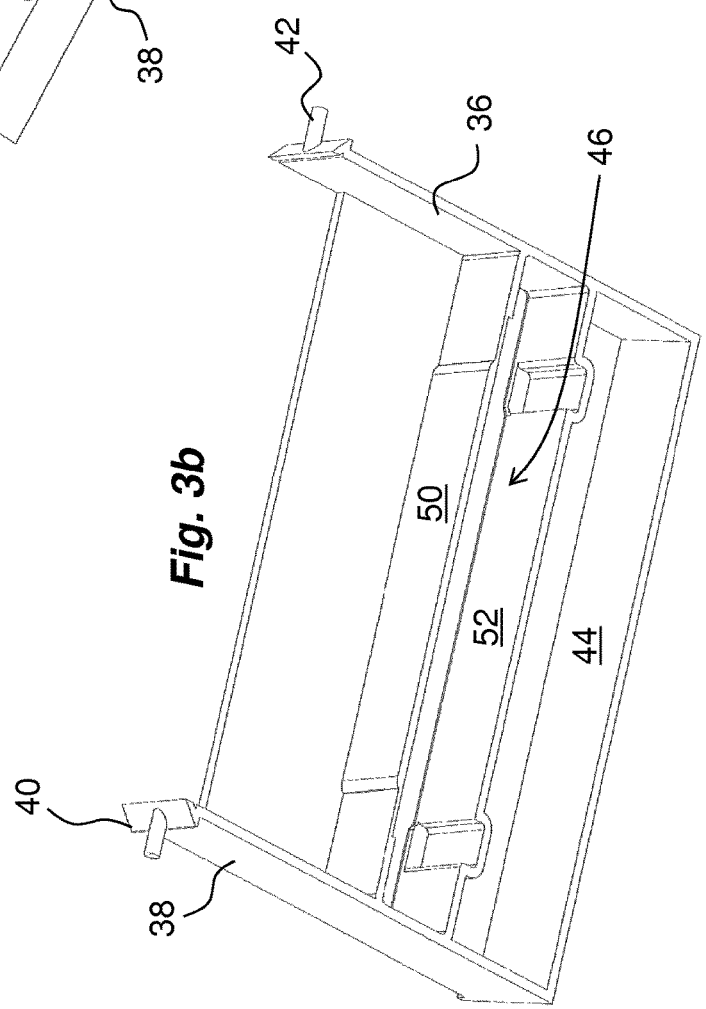

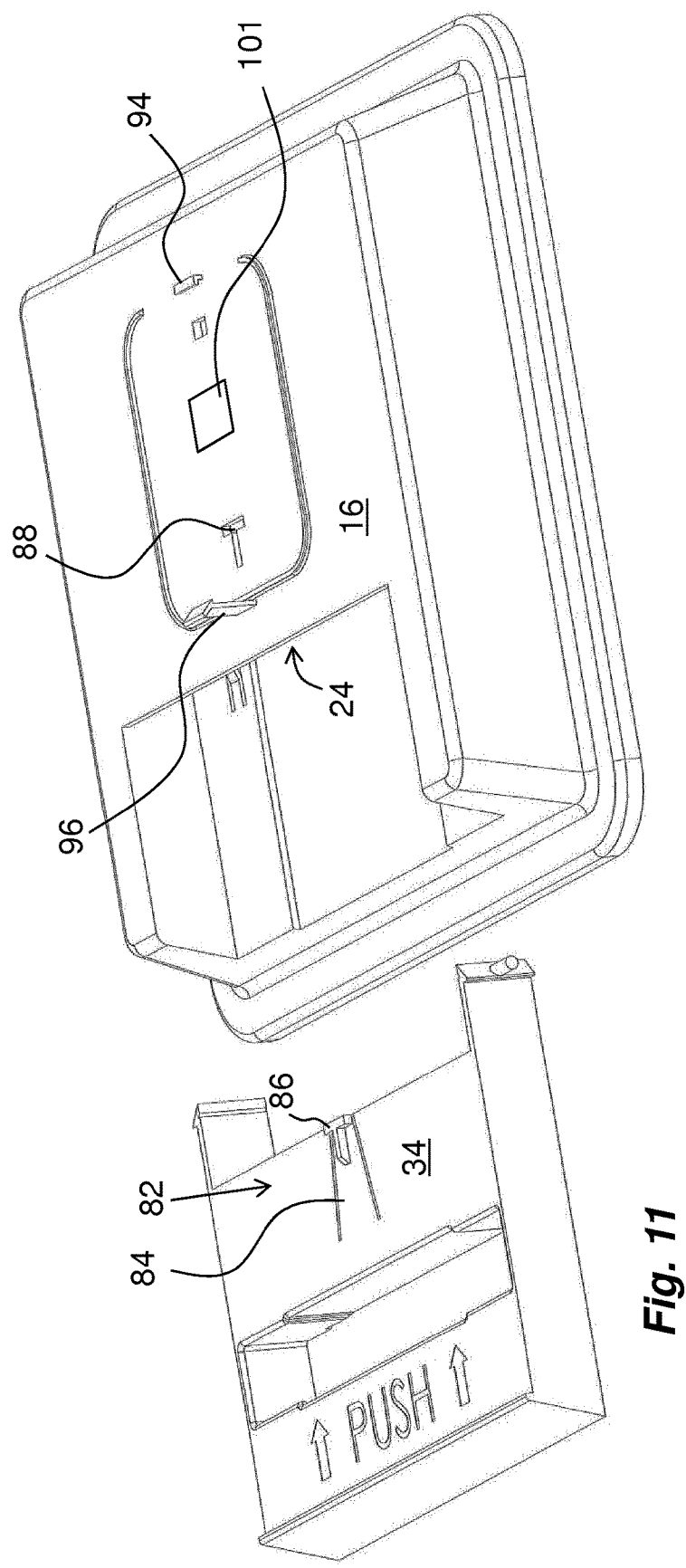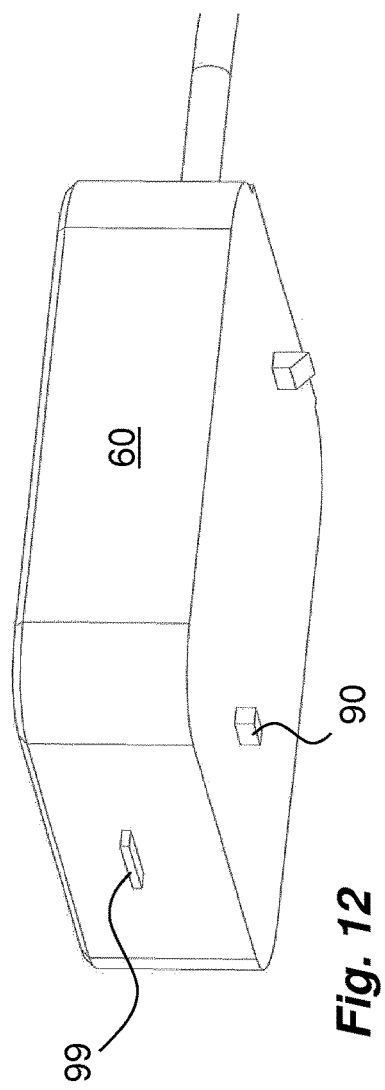
Fig. 11
Fig. 12

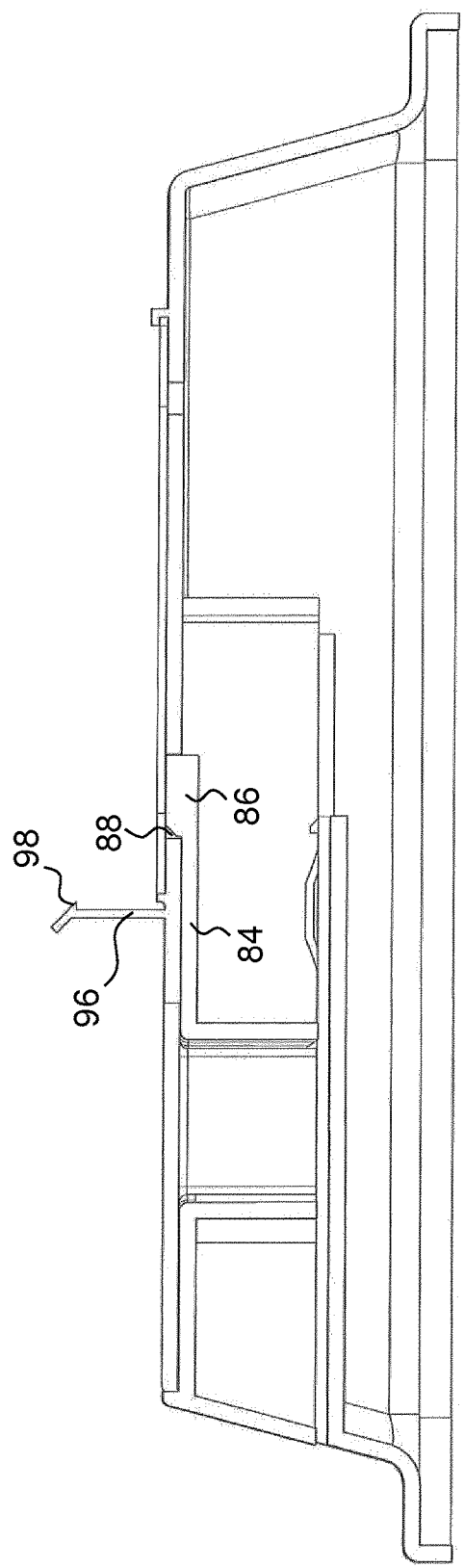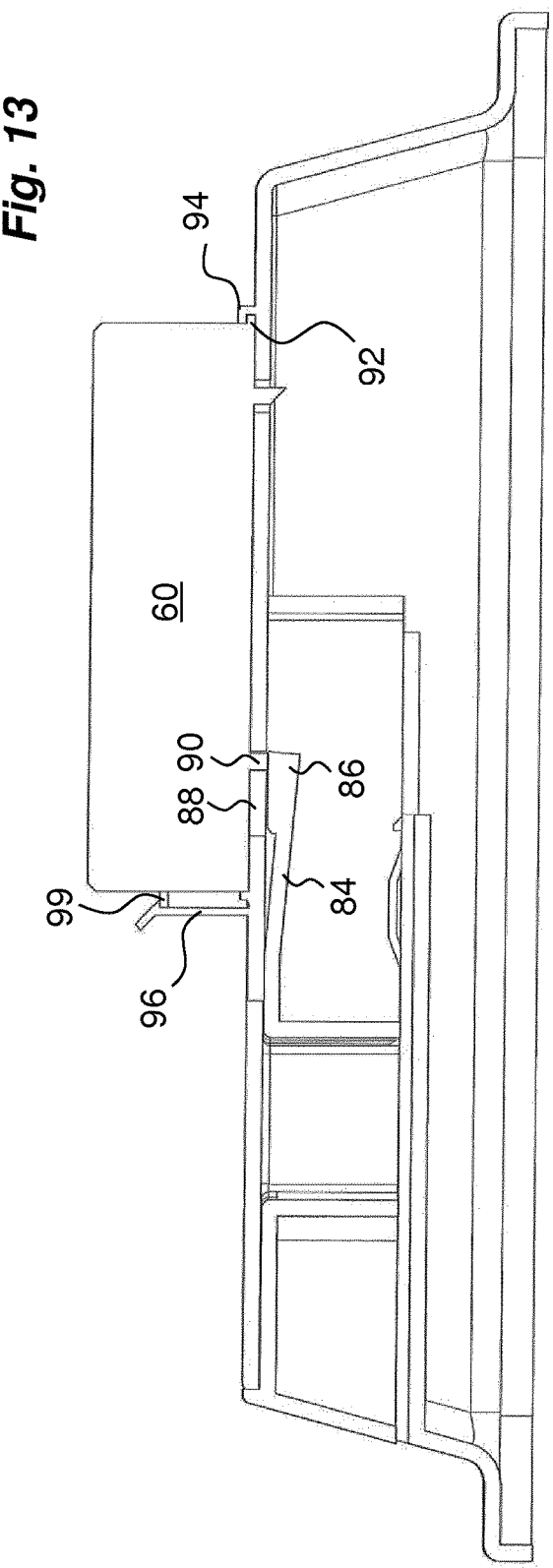

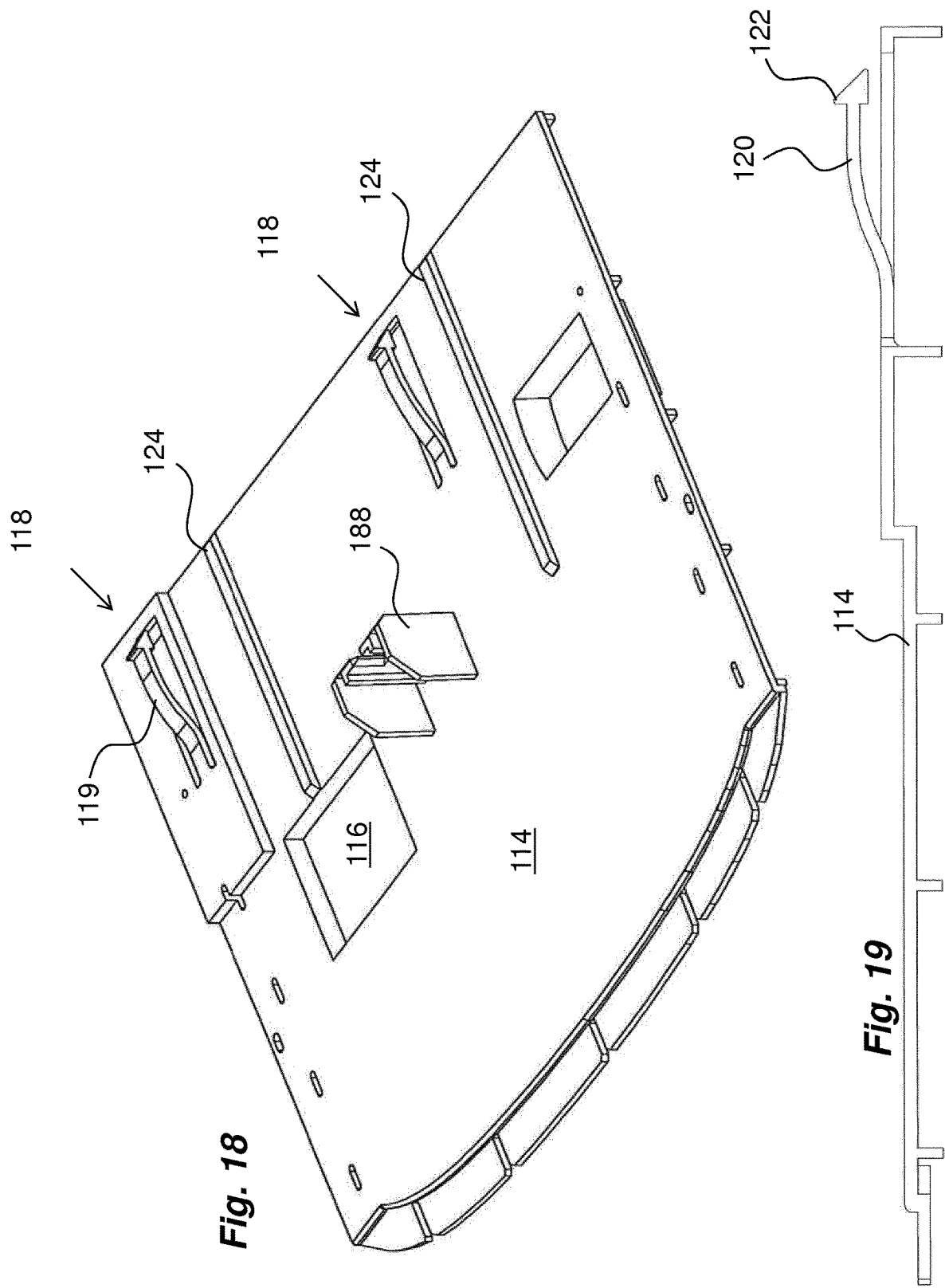

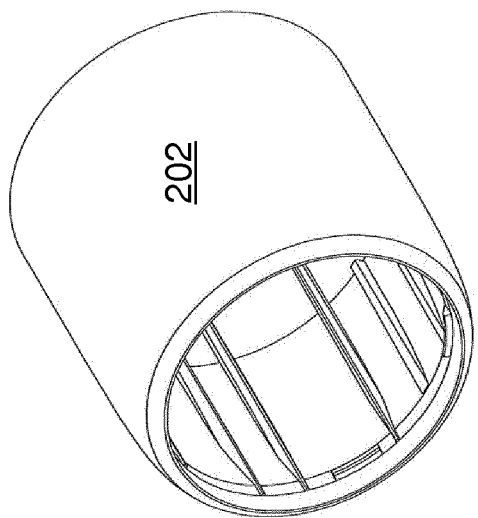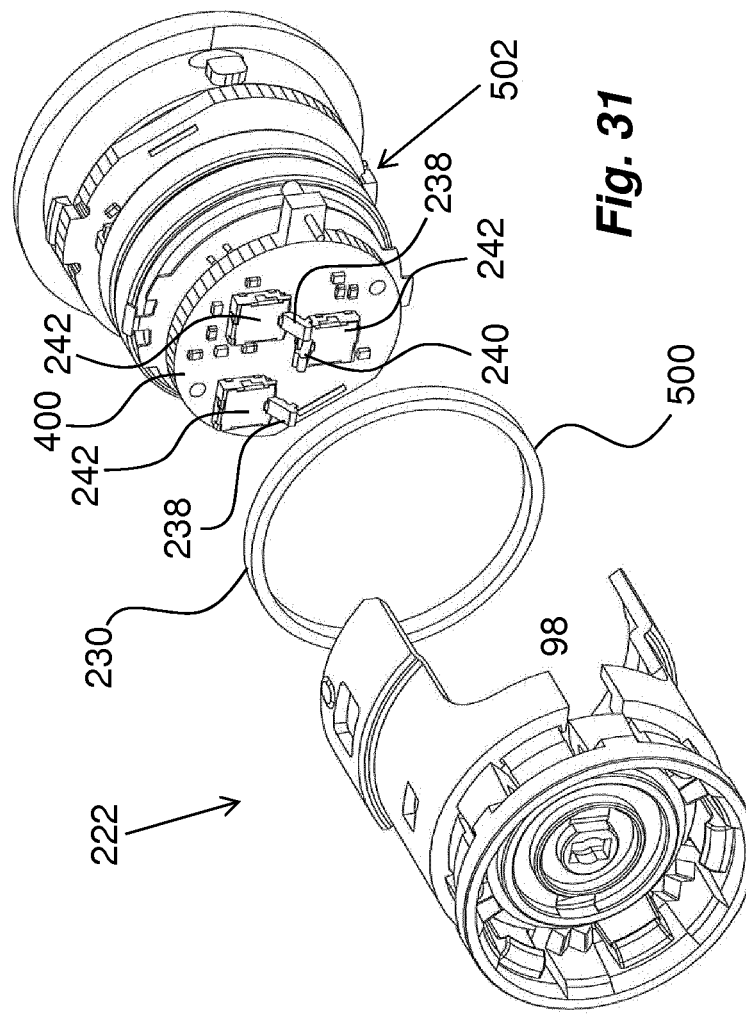
Fig. 31

DEVICE FOR HANDLING MEDICAL WASTE PRODUCTS

CROSS REFERENCE TO RELATED APPLICATIONS

The present application is a U.S. National Phase Application pursuant to 35 U.S.C. § 371 of International Application No. PCT/EP2016/057897 filed Apr. 11, 2016, which claims priority to European Patent Application No. 15164267.5 filed Apr. 20, 2015. The entire disclosure contents of these applications are hereby incorporated by reference into the present application.

TECHNICAL AREA

The present invention relates to a device for handling medical waste products and in particular used medicament delivery devices that are to be discarded in a safe way.

BACKGROUND OF INVENTION

Monitoring aspects of self-administration is becoming more and more important from several aspects. One aspect is that many physicians would like to have more information regarding how a patient is handling the administration of drugs, especially if the patient is following a treatment scheme. In many cases the physician has to rely on what the patients are telling, which may or may not be actually according to the truth. This gives an uncertainty as to how well the patient is responding to the treatment. For instance, if the patient misses several occasions when a dose was to be administered, or administers doses too unregularly, too close to and/or too far to a previous dose, then this may adversely affect the treatment, which could be misinterpreted that the treatment scheme and/or the medicament is not good. In that respect, it might be that the patient does not want to tell the physician that he/she has not followed the scheme and may even discard medicament delivery devices that have not even been used in order to conceal that the treatment scheme has not been followed.

Some solutions to monitor user behaviour have been directed at not having the device as such performing any monitoring or recording when the device is being used but to utilize other equipment that is used in connection with medicament delivery devices. One such equipment is a sharps bin that is required when handling medicament delivery devices arranged with injection needles that may cause injuries such as unintentional needle sticks. The user is requested to discard the medicament delivery devices as soon as possible in a safe sharps bin.

The use of a sharps bin may be utilized for obtaining information regarding the user's behaviour. The use of a sharps bin instead of monitoring by the device as such is an advantage in that the medicament delivery device needs not be modified in order to be able to monitor, record, store and/or transmit information regarding the use of the medicament delivery device.

One solution incorporating a sharps bin is disclosed in the document WO 2014/204958. The document discloses an apparatus for obtaining information from used medical waste products such as medicament delivery devices before they enter the sharps bin. According to a favourable embodiment, the apparatus will have a section or compartment before the sharps bin comprising a sensor that is capable of recording date and time and specifically by creating an image of the medicament delivery device passing the sensor. The sensor is then capable of transmitting the captured information wirelessly to a communications device by different technologies such as RFID, NFC, Bluetooth, etc. Also Ethernet lines or WiFi devices may be used.

The apparatus according to WO 2014/204958 is rather complicated in view of the function and the information obtained. The image creating sensor or camera is an expensive solution for providing a time stamp of the discarding of a used medicament delivery device. It is stated that the image sensor is capable of detecting specific types of waste, but it is very unclear how this may be done or for what purpose. The apparatus has further no blocking elements or the like preventing other objects from being thrown into the sharps bin.

BRIEF DESCRIPTION OF INVENTION

The aim of the present invention is to remedy the drawbacks of the state of the art solutions. This is done by a device according to the features of the independent patent claim. Preferable embodiments of the invention form the subject of the dependent patent claims.

According to one aspect of the invention, it comprises a device for receiving and handling specific medical waste products to be stored in a safe container. The medical waste products could comprise a number of different devices that need to be discarded in a safe way after use, so that they cannot cause injuries or sickness if handled wrongly. Especially medicament delivery devices provided with sharp objects like injection needles are required to be discarded in a safe container as soon as possible after use.

In order to handle medical waste products, the device may comprise a receiving mechanism arranged with a compartment for receiving a medical waste product. The compartment is operably arranged to be moved from a first position wherein a medical waste product may be entered into said compartment to a second position wherein the medical waste product is entered into the safe container. Thus, the medical waste product has to be placed in the compartment in order to discard it into the safe container. Thus, the medical waste product is not touched by a person when discarded into the safe container.

Further, in order to prevent throwing of other objects into the safe container, there may be least one locking element operably arranged to lock the compartment in said first position. In order to unlock the compartment, the at least one locking element may be configured such that a medical waste product placed in said compartment constitutes a keying element for unlocking said compartment. This has the advantage that the shape of the medical waste product is utilized for unlocking of the compartment and thereby enabling a discarding of the medical waste product.

Further, the device may preferably comprise a monitoring unit comprising a detection mechanism which is capable of detecting that the compartment has been moved from the first position to the second position. This feature enables a monitoring of the user behaviour in that the monitoring unit can detect when a medical waste product is discarded and since the medical waste product constitutes a keying element it is ascertained that the information from the monitoring unit contains data regarding discarded medical waste product only because no other waste product can unlock the compartment.

In order to provide the keying function, the compartment may be designed with a form generally corresponding to the shape of the specific medical waste product to be stored in the safe container. The overall shape will then function as a keying form and preferably the at least one locking element comprises at least one contact surface, which at least one contact surface is arranged to be engaged by an outer surface of the specific medical waste product for unlocking the compartment.

According to one favourable solution, the locking element may comprise at least one flexible arm, wherein the at least one flexible arm is arranged with the contact surface. Further, the flexible arm may further comprise a stop ledge arranged to act on the compartment for providing a lock against movement. This solution provides a robust and yet simple locking solution.

In order to prevent any other waste from being thrown into the safety container when the medical waste product is entered into the safety container, the device may further comprise a blocking element arranged to block access to the compartment when in the second position. Further, depending on the desired design of the device, the receiving mechanism may be designed to provide a linear motion and/or a rotary motion of the compartment from the first position to the second position.

Regarding the monitoring unit, it may comprise an electronic circuit capable of providing a triggering signal each time the detection mechanism is operated. This triggering signal may have a number of different functions. One feasible function is that it produces a time stamp. A time stamp is an effective way of providing information regarding the adherence of a user to a treatment scheme and since the user is requested to discard the medical waste product, and in particular an injector, the time stamp provided by the electronic unit is accurate enough in relation to the actual dose delivery. Preferably the electronic circuit may further comprise storage means capable of storing the time stamps for later retrieval and processing.

In order to be able of retrieving and processing the information and the time stamps, the monitoring unit may further comprise a communication unit, operably arranged to communicate information that the receiving mechanism and thus the detection mechanism has been operated to external information receivers, such as time stamps. According to a favourable solution, the communication unit may comprise a wireless communication circuit, and in that regard, the wireless communication circuit may be designed to communicate via near range communication technologies, cellular radio communication networks and/or local area networks. The wireless communication technologies provide easy setup and transmittance of the data from the monitoring unit to appropriate receivers.

In addition, the electronic circuit may further comprise user alert elements, wherein the electronic circuit is arranged to activate the user alert elements at certain time intervals. In that regard, the electronic circuit may be arranged to calculate the time intervals based on the time stamps. The alerting is then performed for informing the user that it is time to administer a dose of medicament. Thereby, the user does not have to keep track when to use a medicament delivery device, this may be done by the monitoring unit. The user alert elements may comprise visual, audible or tactile elements. Preferably, the device is arranged with a releasable attachment of the monitoring unit. Thereby it is easy to replace a full safety container with a new, empty safety container.

According to a further aspect of the invention, the monitoring unit is preferably arranged with an attachment mechanism provided with a mechanical interface, which mechanical interface is arranged to interact with a mating mechanical interface arranged on the receiving mechanism. The arrangement with mating interfaces enables a number of advantages. One advantage is that a firm connection may be obtained between the monitoring unit and the device for handling medical waste products, at the same time as the monitoring unit may be detached and used on other devices for handling medical waste products, for instance when a full device is sent for waste destruction and a new device is received.

The mating mechanical interfaces may also be arranged and designed with specific and unique features enabling only mating of specific monitoring units with specific devices for handling medical waste products. This may be an important feature if a user is provided with a number of monitoring units, where some are used also in connection with medicament delivery devices. With unique connection features it is avoided that a wrong monitoring unit is connected to the wrong device. There would otherwise be a pronounced risk of retrieving unreliable data if it was possible to connect a monitoring unit to any device such as medicament delivery device or device for handling medical waste products.

According to one solution in that respect, the mechanical keying elements may comprise protrusions and recesses arranged in predetermined patterns. The mechanical keying elements may also comprise teeth. These protrusions and recesses may be used further in that activation switches may be positioned such in said interface that they are mechanically activated by said protrusions. Then the protrusions may act directly on the activation switches for activating the monitoring unit such that it is ready for collecting information such as disposal of a medicament delivery device in the device for handling medical waste. One feasible solution is to have the activation switch comprise at least one electrical switch operably arranged to activate the monitoring circuit. Thus, closing the switch will close a power circuit to the monitoring circuit, which will start the monitoring sequence.

Preferably the activation switch is arranged to be activated during operation of the device for handling medical waste products, and more preferably the activation switch is arranged to be activated during operation of the device for handling medical waste products and/or to be activated at the end of a medicament delivery device discarding operation.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 2-4 are detailed views of components comprised in the receiving mechanism, FIGS. 11-14 show a variant of the device of FIG. 1, FIGS. 16-27 show detailed views of the device of FIG. 15, FIGS. 28-31 show a monitoring unit to be used with the device of FIG. 15, FIGS. 32, 33 and 39 show cross-sectional views of the monitoring unit of FIG. 28 in different functional states.

DETAILED DESCRIPTION OF THE INVENTION

Figure 1:
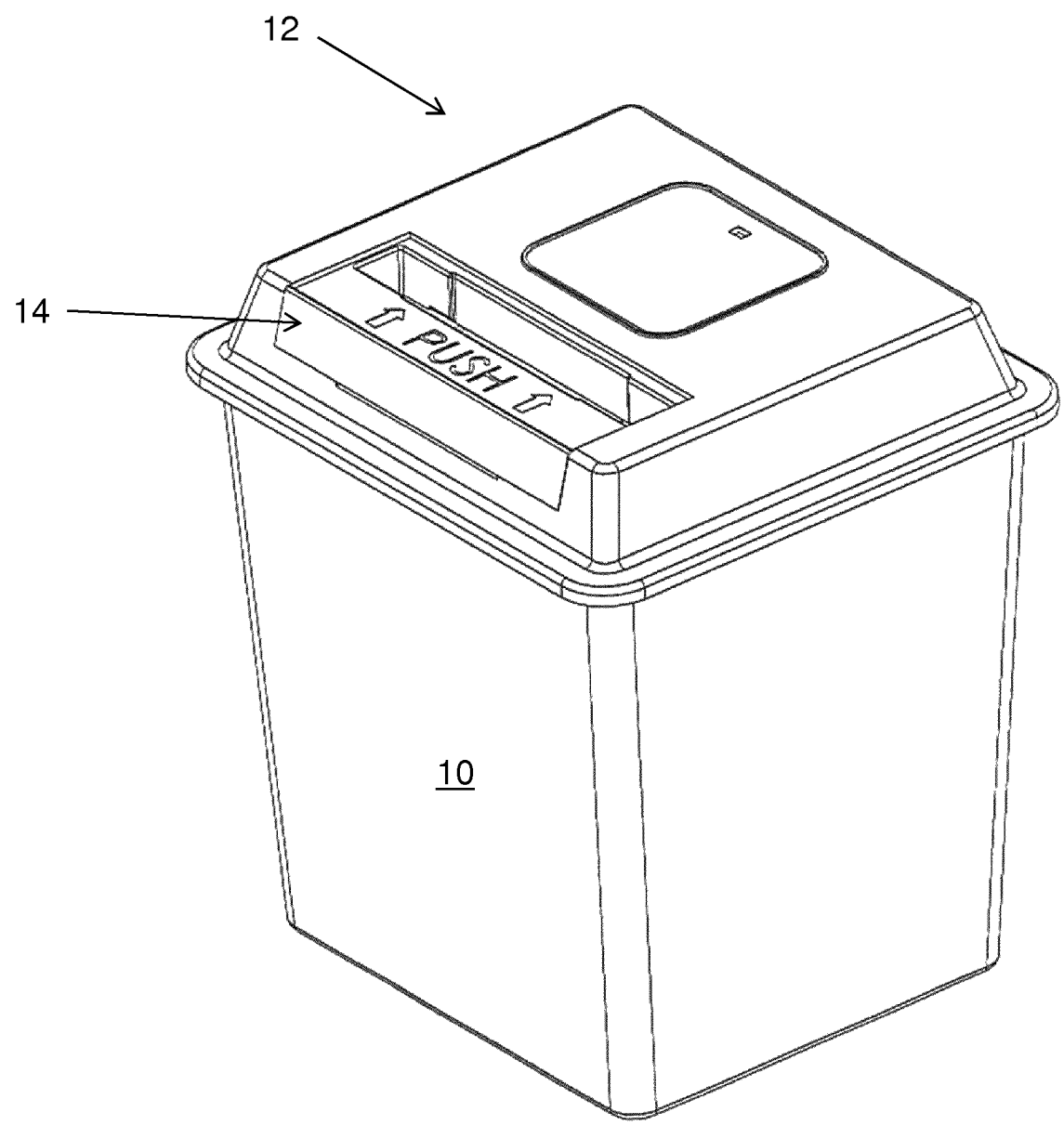
FIG. 1 is a perspective view of a medical waste products container comprising an upper part having a receiving mechanism.
Figure 5:
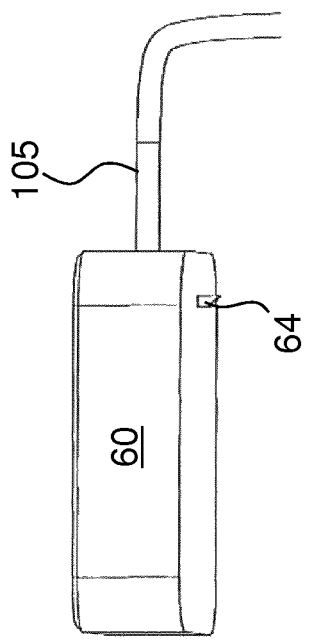
FIG. 5 is a view of a monitoring unit intended to be connected to the upper part.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication.

The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, but in particular medicament delivery devices that may cause injuries or be harmful if not handled properly, especially after use.

The device according to the invention may be used in connection with an ordinary container 10 for medical waste comprising sharp objects such as medicament delivery devices, a so called sharps container or sharps bin. The upper part 12 of the sharps container, for instance a lid, is provided with a receiving mechanism 14 for medical waste products such as medicament delivery devices. It is however to be understood that if an attachable part is provided such as a lid, then there has to be attachment elements that securely holds the lid to the container. Alternatively, the receiving mechanism 14 may be integrated with the container to one unit.

In this respect, the upper part 12 is provided with a generally flat top area 16, FIG. 2a. In the top area, a generally rectangular recess 18 is arranged, having a bottom 20, which recess 18 is arranged with two opposite side walls 22 and a generally rectangular opening 24 into the upper part. Further the bottom 20 of the recess as well as the side walls 22 extend a certain distance into the opening 24 under the top area 16. The recess 18 ends at a side surface of the upper part 12. Further, the bottom 20 of the recess 18 that is extending into the opening 24 is provided with first locking elements 25, FIGS. 2b and 2c, that in the embodiment shown are designed as at least two arms 26, which arms 26 are extending generally parallel with the bottom 20 of the recess 18 into the opening. However, the arms 26 are provided with a convex or raised mid-section 28 as seen in a vertical direction, FIG. 2c. Further the free ends of the arms 26 are arranged with upwardly extending hooks 30. Further, inner surfaces of the side walls 22 of the recess 18 are arranged with attachment posts 32, FIGS. 2b and 4.

Figure 4:
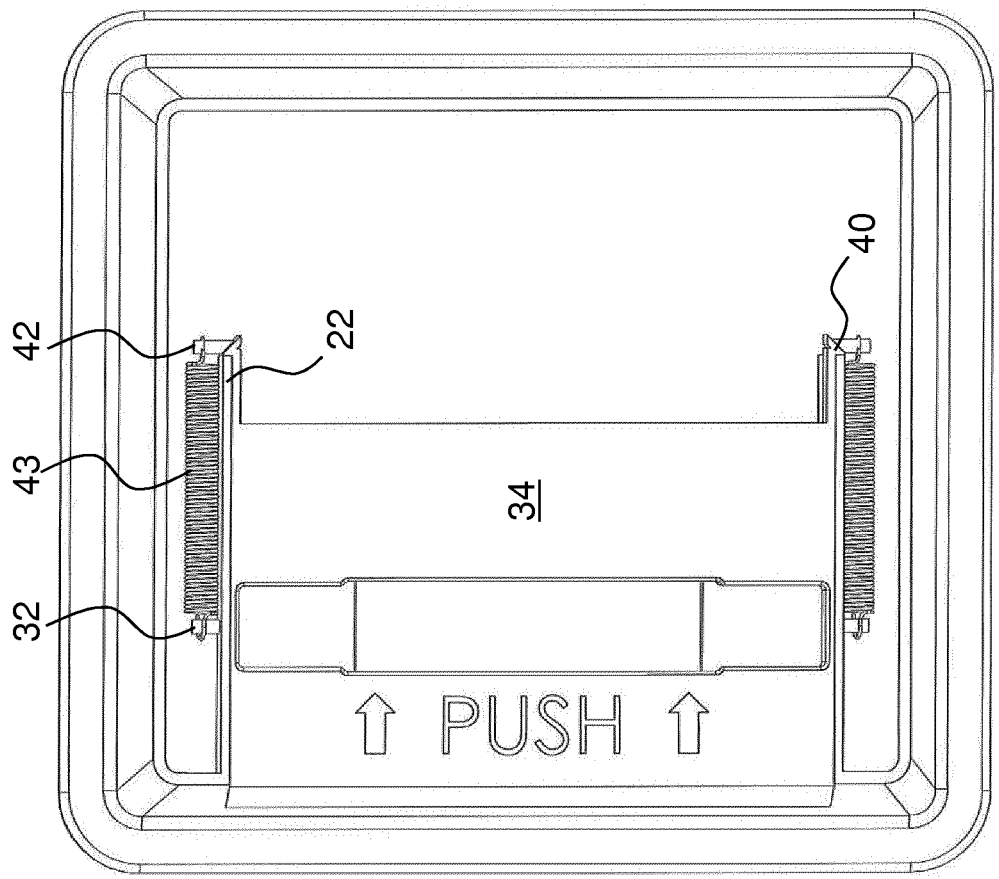

In the recess 18, the receiving mechanism 14 is arranged slidable between a first and a second position, as will be explained. The receiving mechanism 14 comprises a generally flat plate 34, FIG. 3a, that extends into the opening 24 of the upper part and adjacent and generally parallel with an inner surface of the top area 16. Two first and second side walls 36, 38 are attached to or made integral with two opposite edges of the plate 34. As seen in FIG. 3a, the first and second side walls 36, 38 extend further than the plate 34. Also, the inner ends of the first and second side walls 36, 38 are arranged with outwardly extending stop ledges 40 as well as outwardly extending attachment posts 42. Springs 43, FIG. 4, are arranged between the attachment posts for urging the receiving mechanism 14 in the initial first position as seen in FIG. 1, which position is defined by the stop ledges 40 being in contact with end surfaces of the side walls 22 of the recess 18.

A third side wall 44 is attached to or made integral with a third edge of the plate 34 as well as the first and second side walls 36, 38, FIG. 3b. The third side wall 44 is somewhat inclined as seen in FIG. 3a, functioning as a push surface as will be explained, which in an initial position of the receiving mechanism 14, is aligned with a side wall of the upper part as seen in FIG. 1. The third side wall 44 further extends upwards a short distance above the plate 34, FIG. 3a, providing a stop ledge 46 as will be explained. The receiving mechanism 14 is further arranged with a generally rectangular compartment 48 in which used medicament delivery devices are to be placed. The compartment 48 is arranged with a fourth and a fifth long side wall 50 and 52 respectively, extending between the first and the second side walls 36, 38, but is not provided with a bottom. Instead the upper surface of the recess 18 functions as a bottom surface of the compartment 48.

Figure 6:
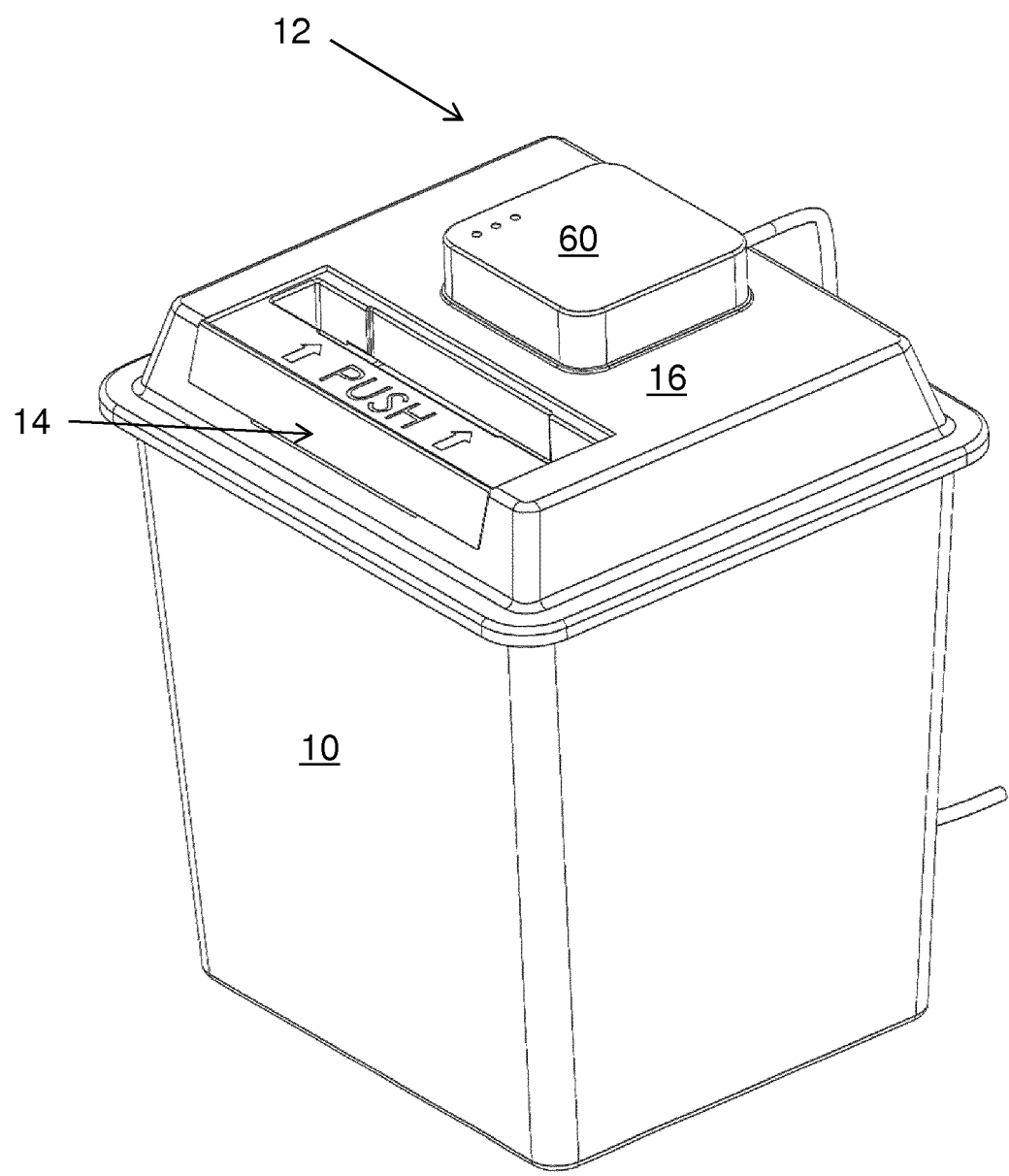
FIG. 6 is a similar view as FIG. 1 but with the monitoring unit attached.

The invention further comprises a monitoring unit 60 that is releasably attachable to the upper part 12 of the container. The monitoring unit is in the embodiment shown designed as a generally rectangular box having a bottom surface shape that is complementary to the shape of the top area 16 of the upper part, FIG. 6. The attachment area of the upper part 12 is arranged with a passage 62, FIGS. 2a, 2b, and the monitoring unit 60 is arranged with a detection mechanism that in the embodiment shown is arranged as a contact element 64 of a detection mechanism 66 that is protruding through the passage 62 and into the interior of the upper part 12 when the monitoring unit 60 is attached.

The device is intended to function as follows. When a patient has administered a dose of medicament from a medicament delivery device MDD, and the medicament delivery device is to be discarded, it should directly be entered into the container for medical waste 10. The medicament delivery device is therefore placed in the compartment 48 of the receiving mechanism 14, where the receiving mechanism is in its initial, first, position. In this respect, the compartment has such dimensions that only medicament delivery devices having certain dimensions can fit therein. Therefore, when a patient is prescribed a treatment scheme with a certain type of medicament delivery device, he/she will also receive a sharps container having a compartment 48 that is adapted to receive the specific medicament delivery device.

Figure 7:
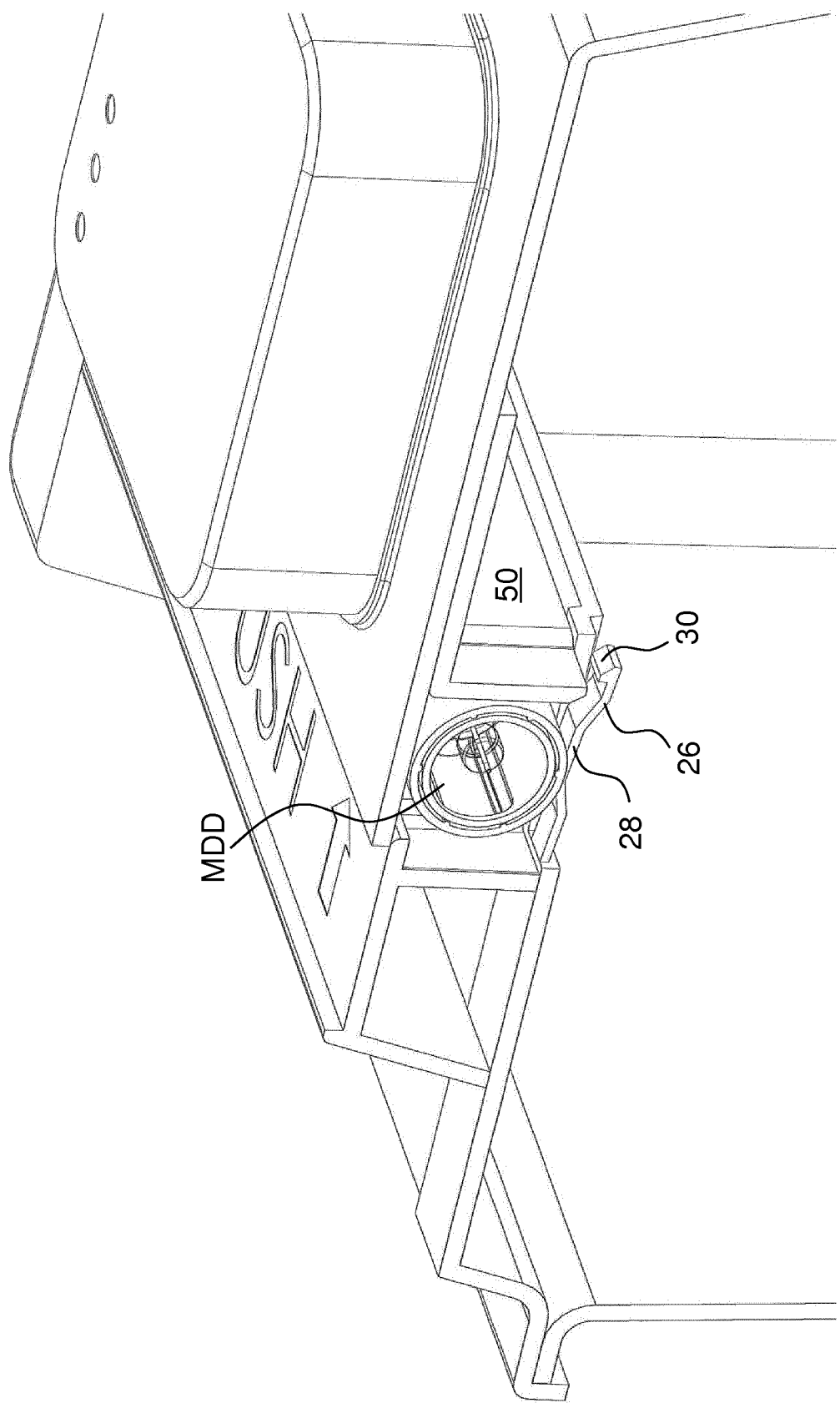
FIGS. 7-10 are cross-sectional views showing different functional stages of the device.

When then a user pushes on the push surface 44, the receiving mechanism with the medicament delivery device MDD placed in the compartment 48 is moved or slid through the opening 24 of the recess 18 and into the interior of the upper part. When the compartment 48 slides through the opening and enters the interior of the upper part, the medicament delivery device MDD will come in contact with the concave or raised mid-sections 28 of the arms 26 such that the free ends of the arms are moved downwards, FIG. 7. This will allow the fourth side wall 50 of the compartment 48 to pass over the hooks 30 of the arms 26 such that the compartment will pass the inner edge of the recess, whereby the medicament delivery device will fall into the container for medical waste 10 in a second position of the receiving mechanism 14, FIG. 8.

Figure 8:
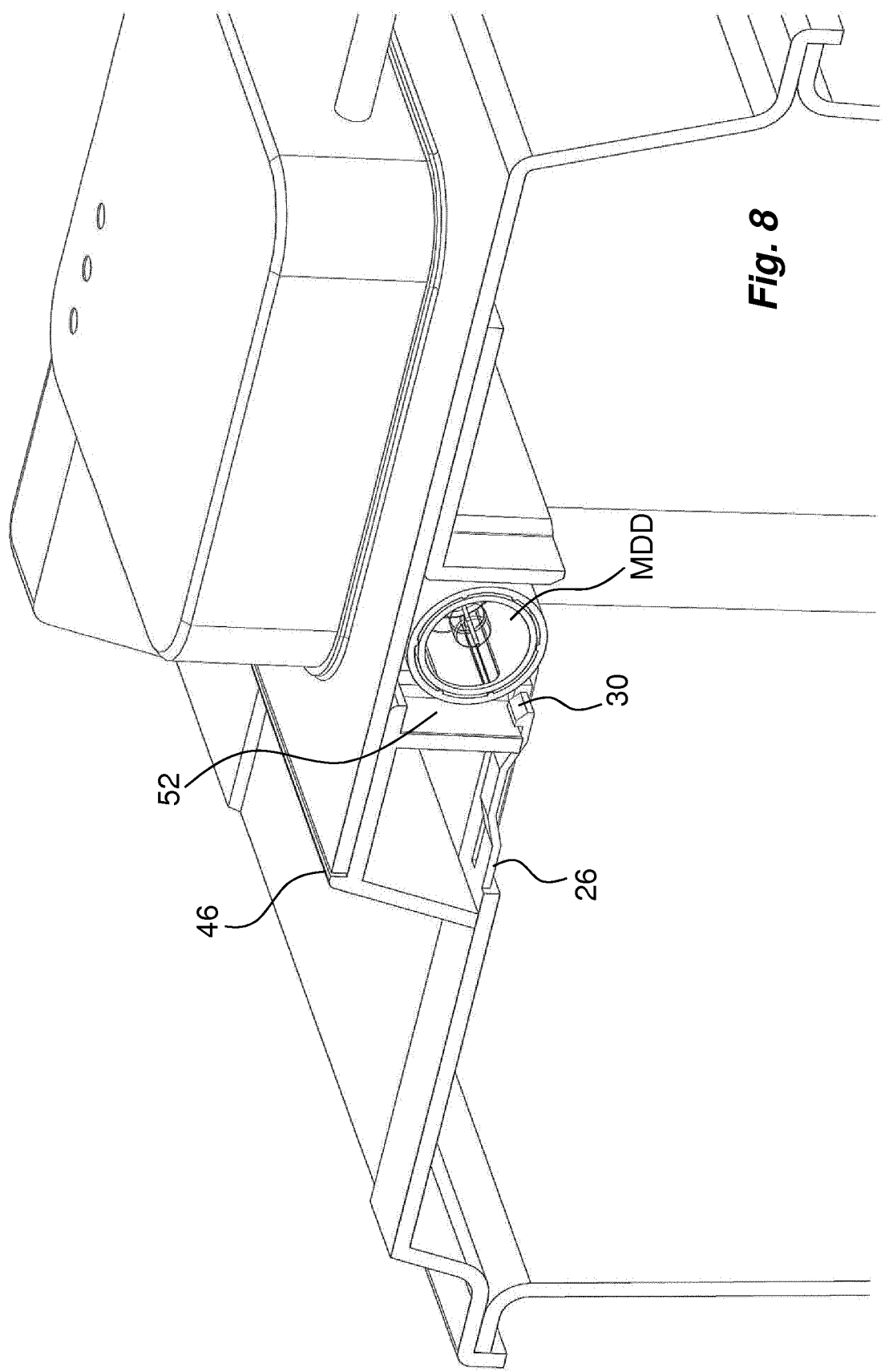

Further movement of the receiving mechanism 14 is prevented by the stop ledge 46 engaging an edge surface of the opening 24 as seen in FIG. 8, as well as by the hooks 30 of the arms 26 engaging the fifth side wall 52 of the compartment 48, as seen in FIG. 8. The latter is because the arms 26 are free to flex upwards again after the medicament delivery device MDD has passed the arms 26. In this second position, the compartment is not accessible because of its position under the top area 16, where the top area 16 acts as a blocking element for accessing the compartment.

When now the medicament delivery device MDD has been discarded, the user may release the receiving mechanism 14, whereby it is moved back to its initial position by the springs 43, FIG. 4. The movement is stopped when the stop ledges 40 hit the end surface of the side walls 22 of the recess 18.

Figure 9:
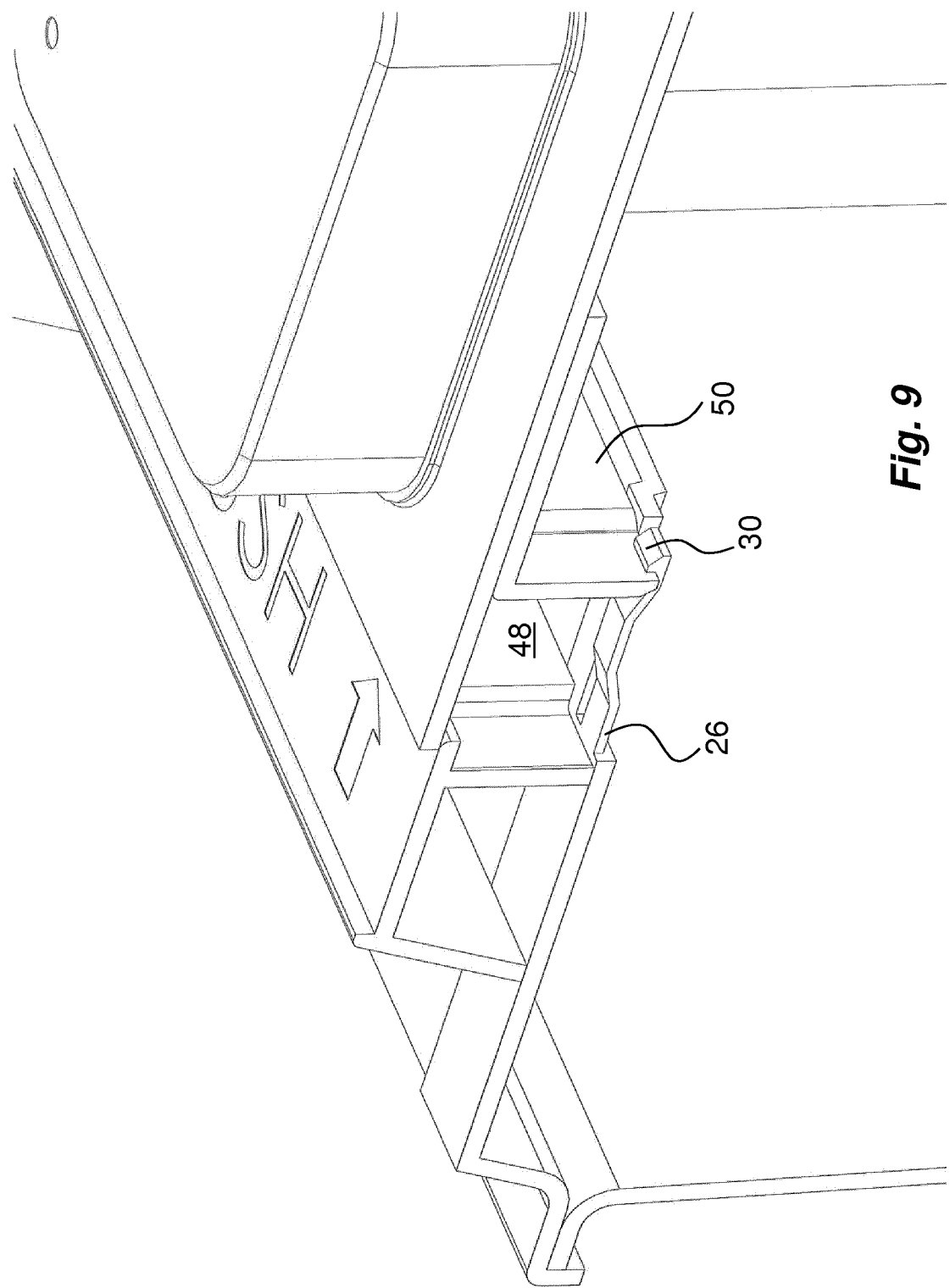

As understood from the above, it is not possible to discard items that are placed in the compartment that cannot affect the arms, because any attempt to push the receiving mechanism 14 into the upper part will be stopped by the hooks 30 of the arms 26 engaging the fourth side wall 50 of the compartment as seen in FIG. 9.

The sharps bin according to the invention has the further function. At the position of the receiving mechanism 14 when the medicament delivery device falls into the sharps bin, the plate 34 has been moved in contact with the contact element 64 of the monitoring unit 60, operating it by pushing it upwards into the monitoring unit, FIG. 10.

Figure 10:
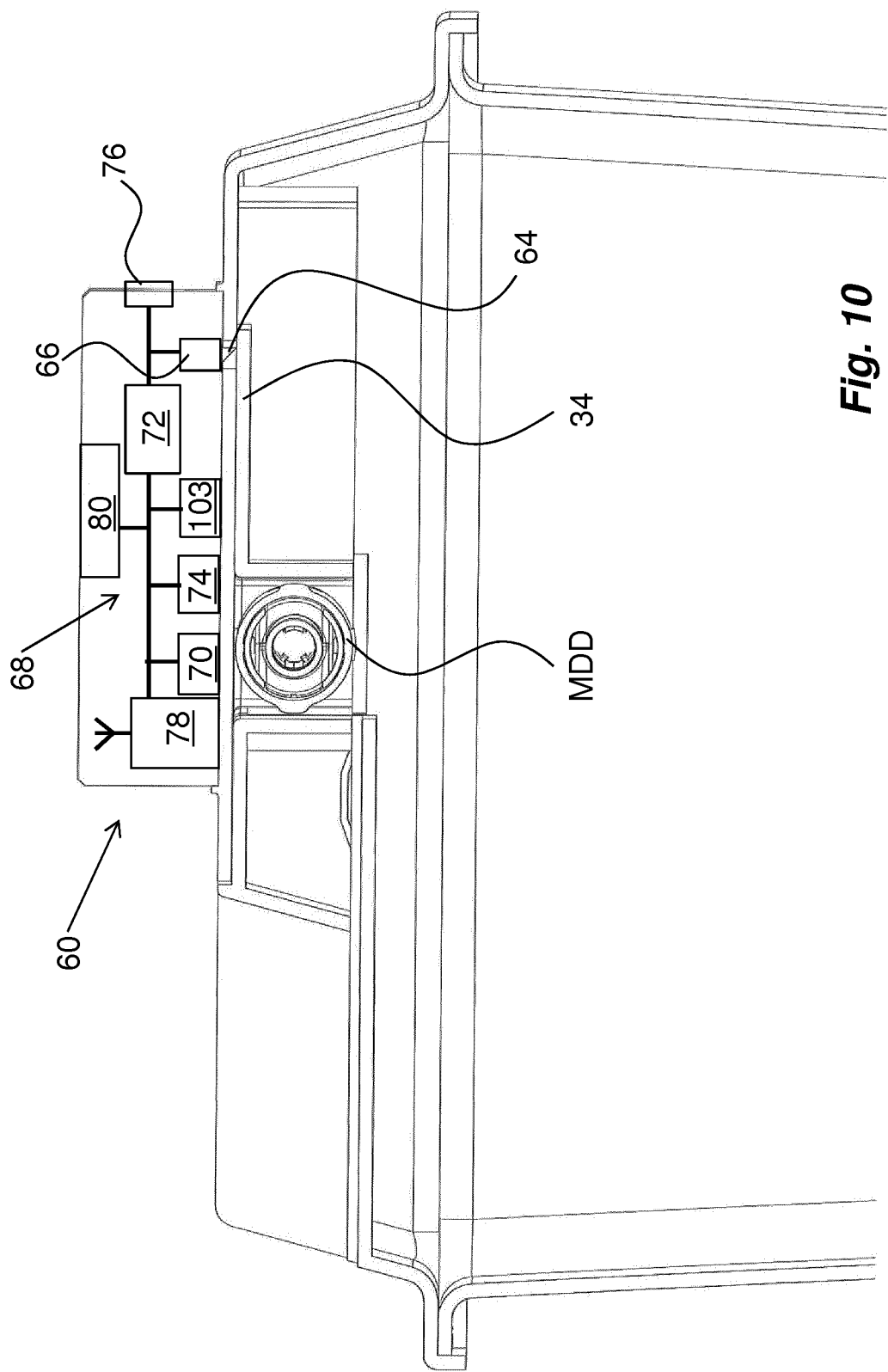

The contact element 64 of the detection mechanism 66 is operably connected to an electronic circuit 68, FIG. 10, which electronic circuit 68 may have a number of functions and features. The electronic circuit 68 is arranged with a suitable power source 70 for its function, which could be batteries, photovoltaic panels, or power from mains. The electronic circuit may further be provided with a processor 72 capable of executing data program code in order to perform various tasks. The data program code may then be stored in appropriate memory elements 74 of the electronic circuit 68. One of the functions or features may for instance be that the processor 72 of the electronic circuit 68 may comprise an internal clock whereby a timer function may be obtained, capable of providing a time stamp of when the contact element has been operated. The time stamp may then be stored in the memory elements 74 of the electronic circuit 68. One or several stored time stamps may then be retrieved by appropriate data retrieving technologies. One such could be an I/O interface 76 with receptacles to which a portable memory may be connected.

The portable memory may comprise a USB memory which may be attached to appropriate receptacles for retrieving the stored time stamps. The USB memory may thereafter be connected to a computer or other smart device that can process the data of the time stamps. In that manner, the patient's usage behaviour over time may be monitored. The usage behaviour may be compared to a prescribed treatment scheme that the patient has received from his/her physician or other medically skilled person, whereby the adherence of the patient will be derived. Any deficiencies in the adherence can then be addressed by the physician of the patient. Other types of portable memories that can be used may comprise MMC-cards, SD-cards, portable hard discs, etc.

Also or instead, a communication cable 105 such as a USB cable may be connected, which cable may be attached to a computer or a smart device with its other end, whereby stored time stamps are transmitted via the cable and handled in the same manner as above. Also, or instead, the retrieved data, either by a portable memory or by cable, may be transmitted by the computer or smart device to remote information storage sources, e.g. on the internet, by using the communication capabilities of the computer or smart device.

Thereby, the user or patient may use his/her own computer or smart device for retrieving saved time stamps and to use appropriate available communication networks for transmitting the retrieved data to a dedicated information source, from which a physician or medically skilled person may obtain and process the data. The physician or skilled person may then use the communication networks transmit information to the computer or smart device of the user regarding the adherence of the patient and to alert or instruct the patient depending on the results.

In this context it is of course possible to include a wireless communications circuit 78 in the monitoring unit 60. The communication technologies available may comprise near range communication technology such as RFID, NFC or the like, as well as Bluetooth, Ant, Zigbee, just to mention a few. If for instance NFC technology is used, then a mobile device being NFC-enabled may derive the stored timestamp data from monitoring unit. The mobile device may then either be capable of handling the data, or may in turn transmit the data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the monitoring unit 60 as such. Then the monitoring unit may communicate directly with external data storage sources, data handling centres etc. via the communication networks. Time stamps may then either be stored locally and transmitted at specific intervals or may be transmitted directly without storage.

A further feature that the monitoring unit 60 may comprise is a usage alert function. With this function, a treatment scheme with specific dates or times or intervals the medicament is to be taken is stored in the monitoring unit. The electronic circuit 68 is then arranged with alerting elements 80 such as light, sound and/or vibration elements that are capable of providing information to the user that it is time to administer a dose of medicament. The electronic circuit is then capable of utilizing the timer to calculate a subsequent administration time.

When the monitoring unit 60 is arranged with a communication technology that enables the monitoring unit to communicate directly with data handling centres via the Internet, then it might suffice if a short triggering signal is transmitted, which triggering signal will be used at the data handling centres for creating the time stamp there. In that respect, any alert signal may be generated at the data handling centre and be transmitted to the monitoring unit. This transmitted alert signal may then activate the alerting elements for providing the user with administering information.

In order to further ascertain that no objects can be entered into the sharps bin without being monitored by the monitoring unit 60, the receiving mechanism 14 may be arranged with a second locking element that is activated by the monitoring unit. This is because someone might discard a medicament delivery device when the monitoring unit is not attached, whereby no registration will occur. FIGS. 11 to 14 show as a variant an example of a second locking element 82. The plate 34 is here arranged with a tongue 84 formed by a cut-out in the plate 34, FIG. 11, having its free end directed in the pushing direction of the receiving mechanism 14. The free end of the tongue 84 is further arranged with a protrusion 86 directed upwards, shaped as a T. The T-shaped protrusion 86 is arranged to fit into a correspondingly shaped passage 88 in the top area 16 when the receiving mechanism 14 is in its initial position as seen in FIG. 1. The monitoring unit 60 is in that regard arranged with a downwardly directed protrusion 90, FIG. 12, that when the monitoring unit is attached to the top area 16 will extend into the passage 88.

Thus, when the monitoring unit 60 is not attached to the top area, the T-shaped protrusion 86 of the tongue 84 of the receiving mechanism 14 is extending into the passage 88 of the top area 16, FIG. 13, which will prevent the receiving mechanism 14 from being pushed into the opening 24. Thus, no medicament delivery devices can be discarded in this state.

However, when the monitoring unit 60 is connected to the top area 16, for instance by a horizontal ledge 92 fitting into an L-shaped protrusion 94 on one side of the monitoring unit 60, and by a flexible tongue 96 provided with an edge 98 in engagement with a ledge 99 on the opposite side of the monitoring unit 60, FIG. 14, then the downwardly directed protrusion 90 of the monitoring unit 60 will fit into the passage 88 of the top area 16, and will press the tongue 84 of the receiving mechanism 14 downwards, whereby the T-shaped protrusion 86 is moved out of engagement with the passage 88, FIG. 14. Thereby the receiving mechanism 14 is released and can be pushed inside the upper part as described earlier.

The upper part of the sharps container may further be arranged with an information carrier 101, FIG. 11, and the monitoring unit may be arranged with reader 103, FIG. 10, of the information carrier. The information carrier may be a bar code, a QR-code, an RFID-tag, an NFC-tag, for instance. The monitoring unit is then arranged with a corresponding reader of bar code, QR-code, RFID or NFC, capable of reading the information carrier when the monitoring unit is attached to the upper part. This solution may be used in order to prevent tampering with the device or faking medicament delivery since the monitoring unit has to be attached in order for instance to function and to record injection history.

Also, the same monitoring unit may be used for a number of different sharps bins for different medicament delivery devices since the monitoring unit is capable of identifying each specific sharps bin from reading the data on the information carrier. The identification of each sharps bin may comprise unique serial numbers of the sharp bins, which serial numbers may be used decommissioning and/or recycling. Added data may then be the number of discarded medicament delivery devices in each sharps bin. In that respect, RFID-tags as information carriers may be advantageous since the reading of the information carriers may be done at a distance between the sharps bin and the information reader.

FIGS. 15-39 display a further embodiment of the invention. In order to facilitate the understanding of the embodiment, the wording proximal and distal is used and is marked in FIG. 15 with Prox. and Dist. respectively, wherein proximal is a direction towards an intended user and distal is the opposite direction. Also the wording up and down are used and marked in FIG. 15 with Up and Down.

Figure 17:
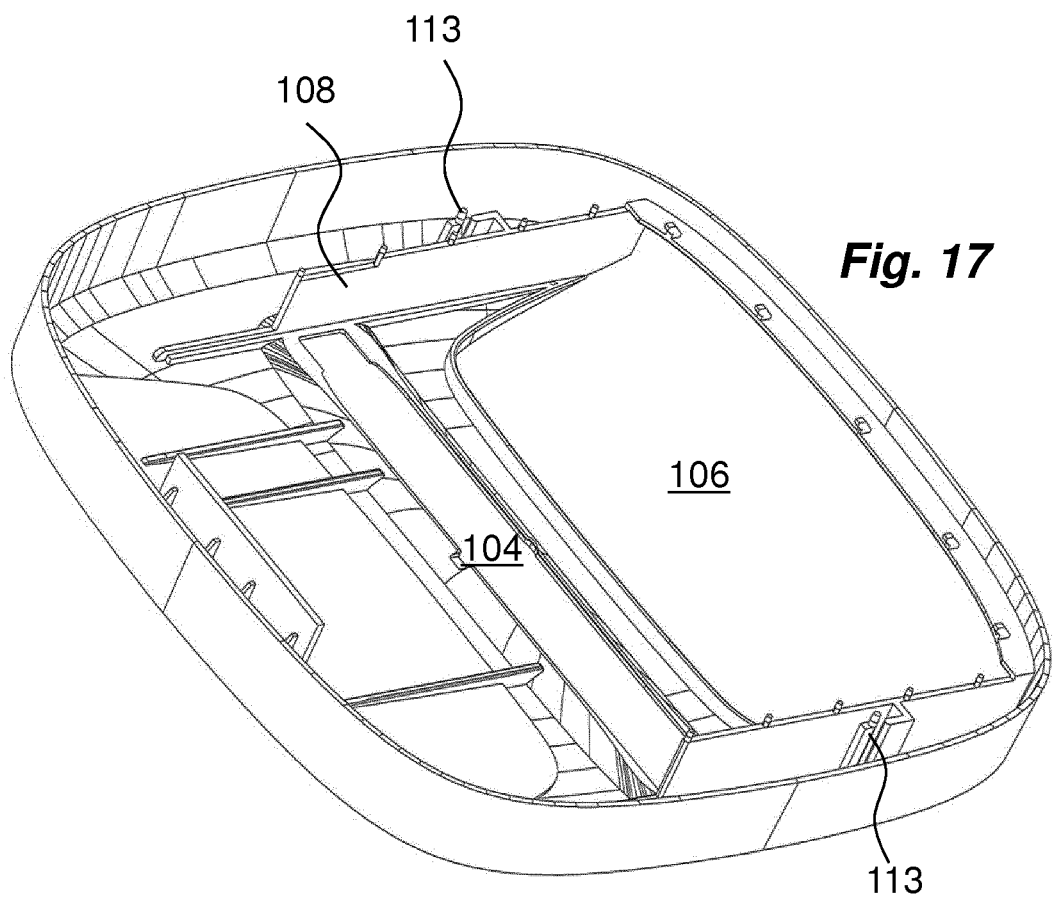

The embodiment comprises a container 100 having a bottom and side walls. An upper part 102 is arranged to be releasably attached to the upper part of the container 100. The upper part is arranged with a centrally positioned first passage 104, FIG. 16, which first passage 104 preferably has a shape that is complementary to a cross-sectional shape of a medicament delivery device to be discarded. An opening 106 is arranged at one edge of the upper part, extending with a somewhat arc-shaped edge. The sides of the opening 106 are arranged with vertically extending side walls 108. A top area 110 of the upper part is arranged with a generally vertically extending ledge 112, positioned on the opposite side of the opening, the function of which will be described below. The top area 110 acts as a blocking element for accessing the interior as will be described. As seen in FIG. 17, posts 113 are placed adjacent each side wall 108, the function of which will be described below.

Further, a bottom plate 114, FIG. 18, is attached to the upper part 102 such that it will constitute a bottom surface of the opening 106 and where an inner end of the bottom plate 114 terminates past the first passage 104 as seen in the distal direction from the opening 106. A rectangular passage 116 is further arranged in the bottom plate 114, the function of which will be described below. Further, first locking elements 118 are arranged that in the shown embodiment comprise two resilient arms 120 that are arranged in the bottom plate 114, having their free ends directed away from the opening in the distal direction, wherein upwardly directed surfaces constitutes contact surfaces 119 as will be described. The arms 120 are curved upwards as seen from the side in FIG. 19, and the free ends of the arms 120 are arranged with upwardly directed, generally vertical, hooks 122. The bottom plate 114 is also arranged with guide ledges 124 extending in a direction from the opening.

Figure 20:
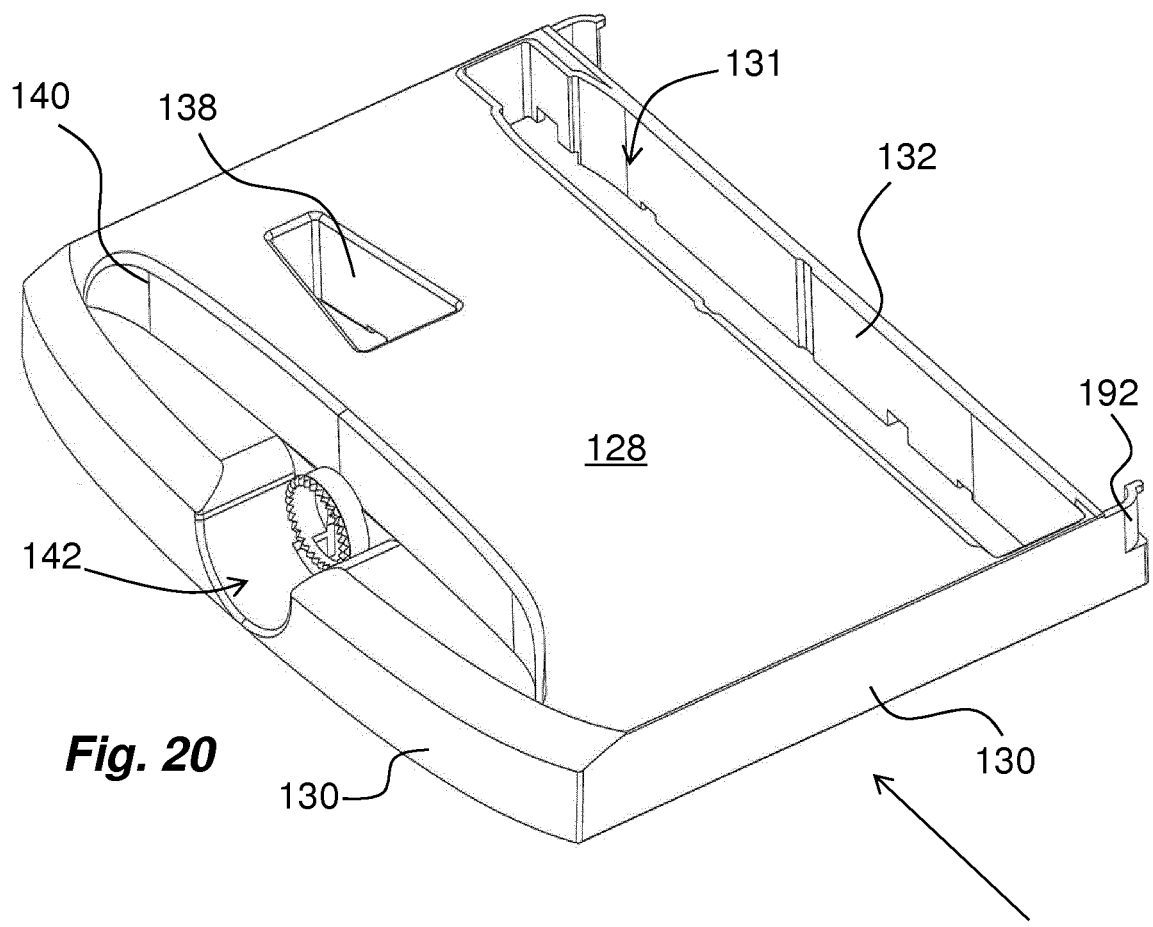
Figure 21:
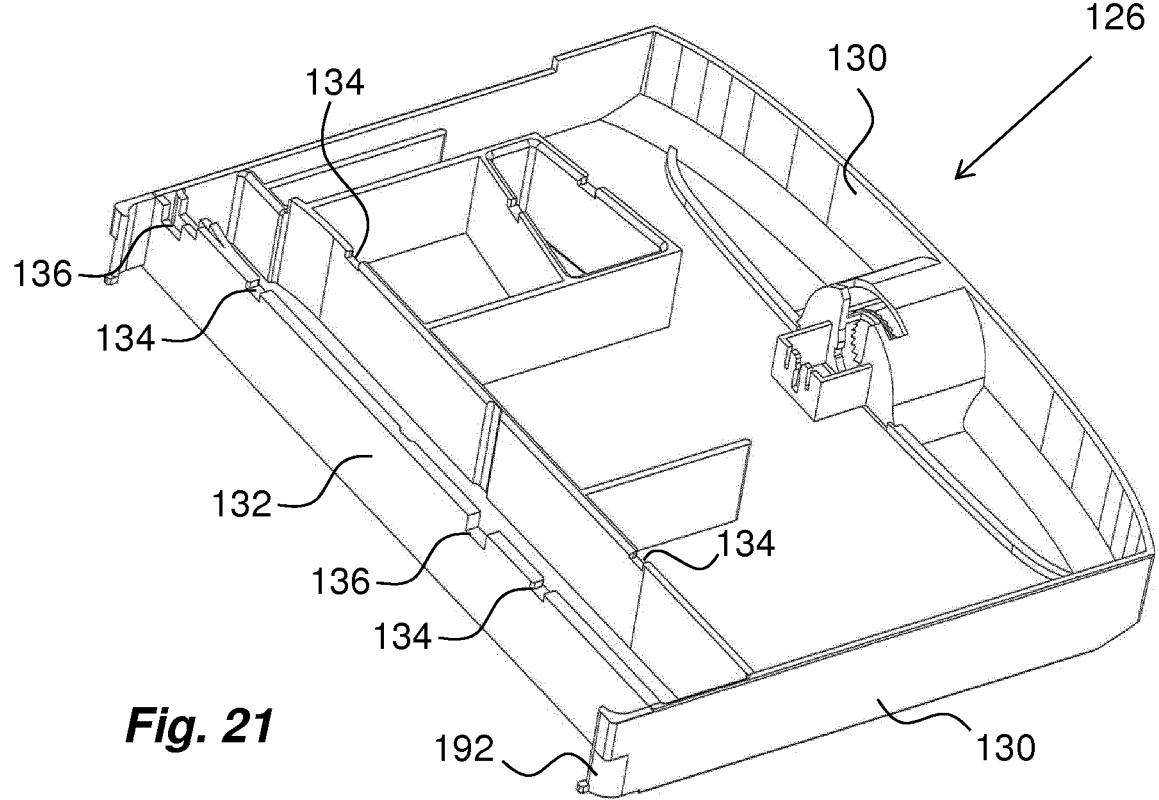
Figure 22:
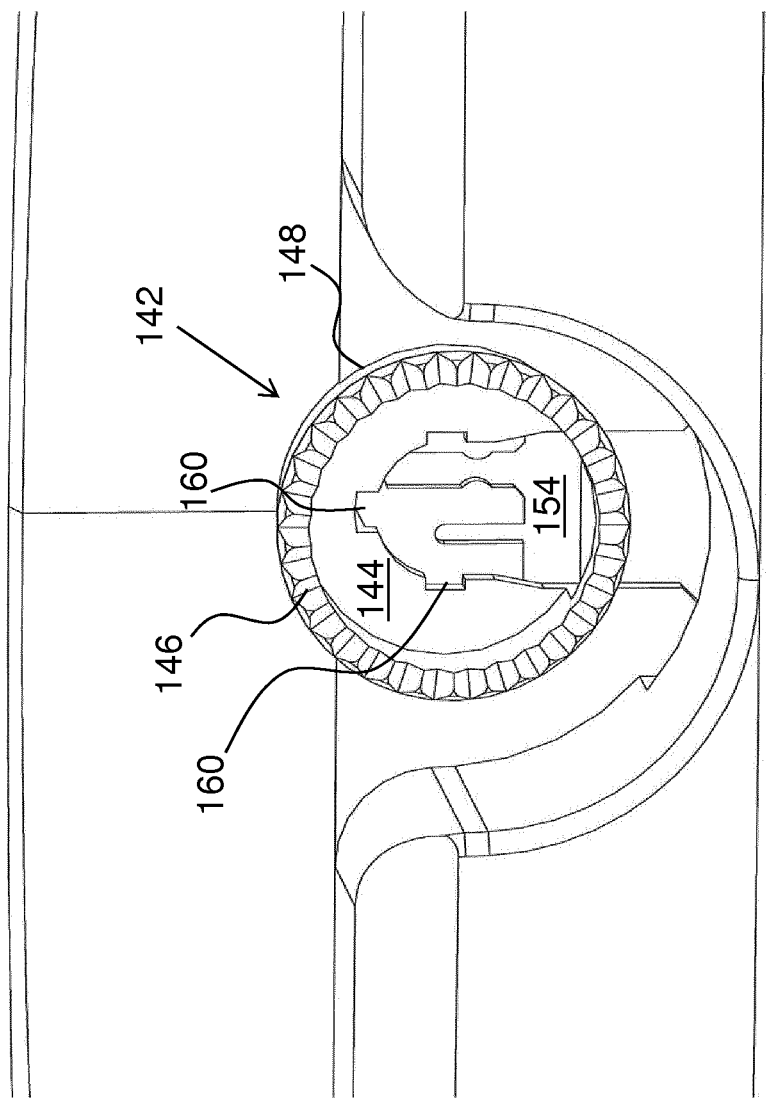

A receiving mechanism 126 is arranged to fit into the opening, FIGS. 20-21. The receiving mechanism 126 comprises a plate 128, FIG. 20, having a width generally corresponding to the width of the opening 106. Along the front and side edges of the plate, generally vertically downwardly extending walls 130 are arranged. A first compartment 131 with vertical side walls 132 is arranged along one side of the receiving mechanism, having dimensions generally corresponding to the length and width of the first passage 104. The lower edges of two of the vertical walls are arranged with first cut-outs 134, FIG. 21, in which the guide ledges 124 of the bottom plate 114 are intended to fit and to guide the receiving mechanism 126 during use, as will be described. Further, the most distal vertical wall 132 is arranged with second cut-outs 136, in which the arms 120 of the bottom 114 plate are intended to fit, as will be described.

Further a second compartment 138 with vertical walls is arranged in the plate 128, FIG. 20, which second compartment 138 has a somewhat cone-shape in the embodiment shown. The plate 128 is further arranged with a vertical ledge 140 as seen in FIG. 20. The receiving mechanism 126 is further arranged with an attachment interface 142, FIG. 22, for a monitoring unit arranged in a proximally facing side wall. The attachment interface 142 is arranged with an annular contact surface 144 provided with a number of protrusions 146 that in the embodiment shown are designed as a number of teeth, the function of which will be described below. An outwardly directed circumferential ledge 148 is further arranged around the teeth.

Figure 23:
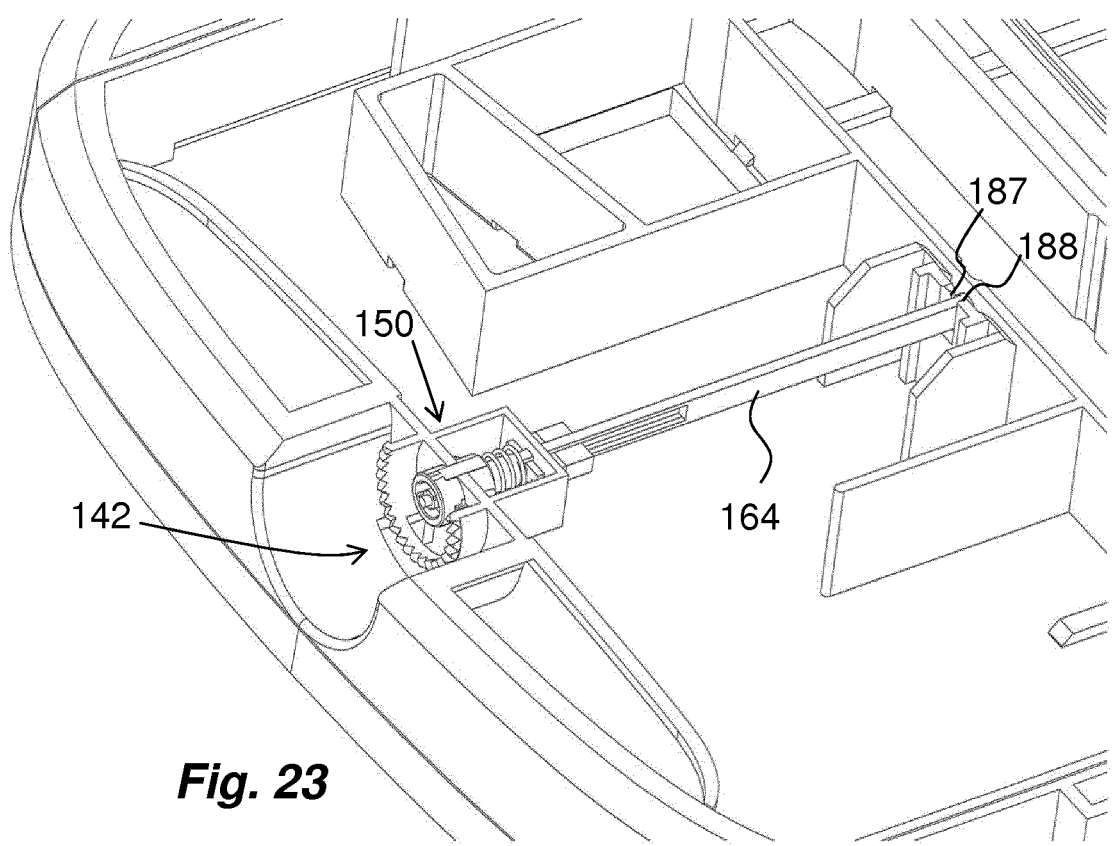
Figure 26:
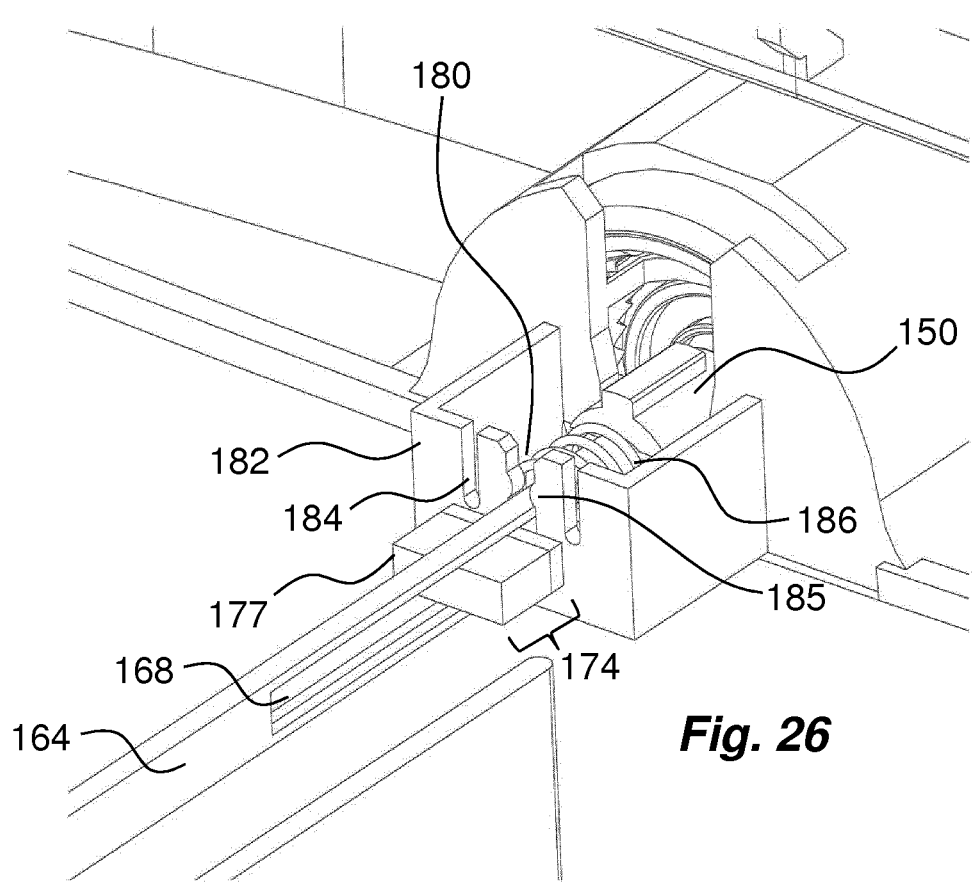
Figure 24:
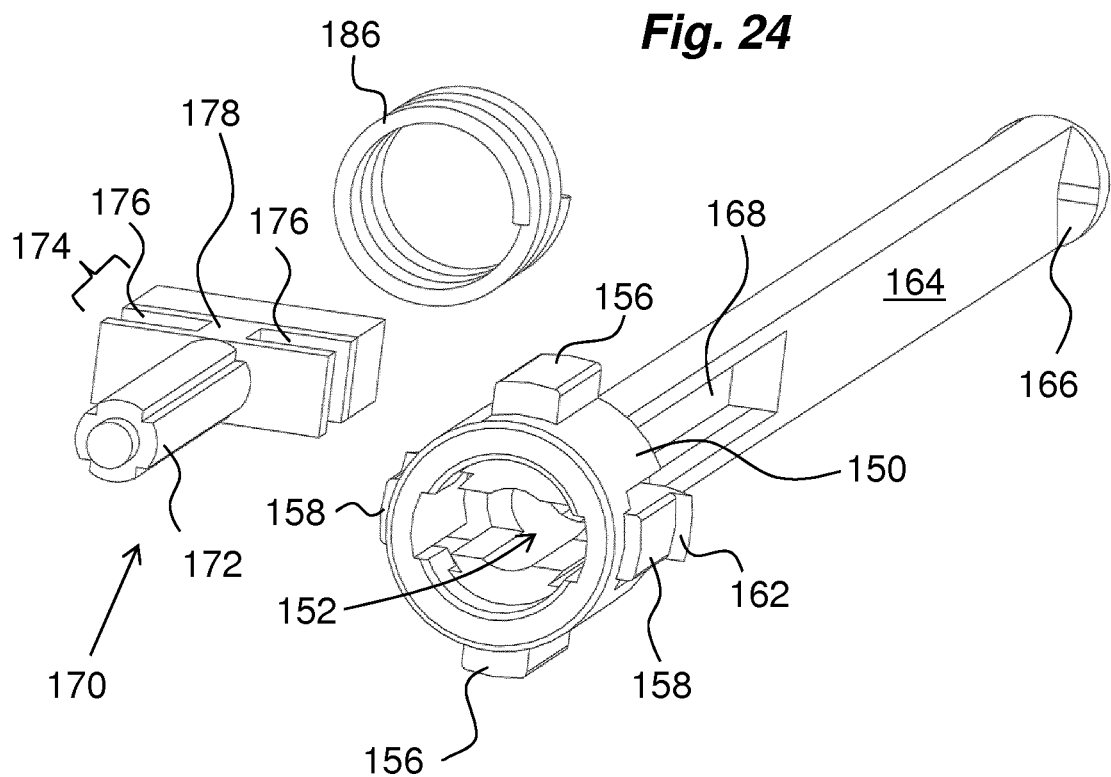
Figure 25:
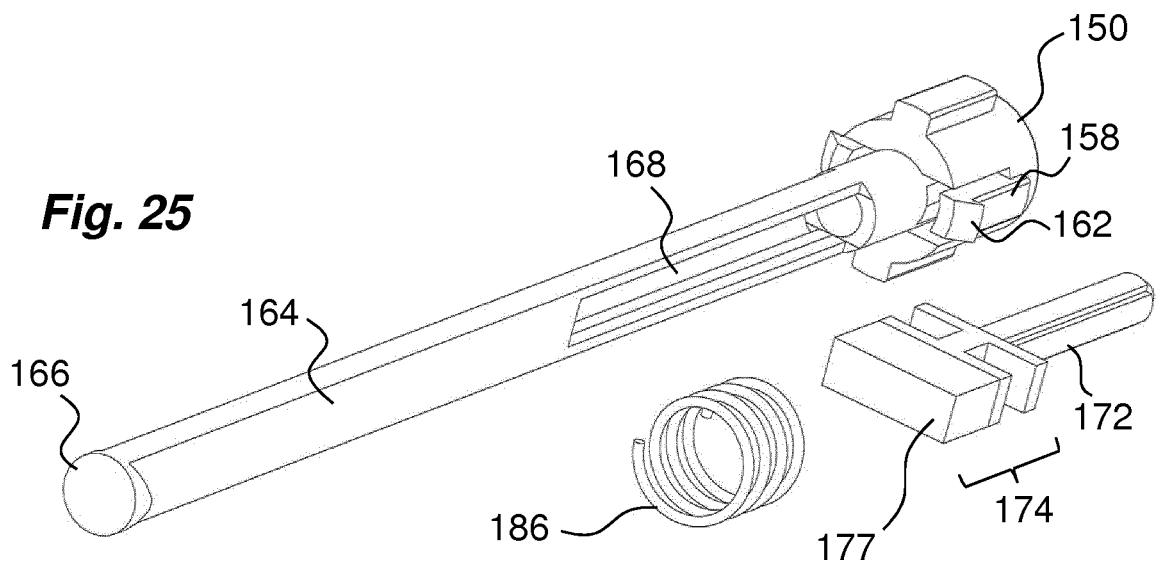

At the centre of the interface a generally tubular interface element 150 is arranged, FIGS. 23-25, which interface element has a central passage 152. The interface element 150 is arranged slidable in the receiving mechanism in that the attachment interface is arranged with a passage 154, FIG. 22, through which the interface element 150 may extend as seen in FIG. 23. The interface element 150 is further arranged with a number of ledges 156, 158 on its outer surface, FIG. 24, which ledges 156, 158 are arranged to fit in cut-outs 160, FIG. 22, of the passage 154 of the attachment interface 142. Two of the ledges 158 are arranged to be flexible in a generally radial direction and are provided with outwardly directed protrusions 162, which protrusions get in contact with distally directed surfaces of the edges of the cut-outs 160 for limiting the movement of the interface element 150 in the proximal direction. The interface element 150 is further arranged with a distally extending arm 164 provided with a generally rectangular cross-section. The distal end of the arm 164 is provided with a generally circular disk 166. A longitudinally extending cut-out 168 is further arranged in a proximal part of the arm 164.

An activator element 170, FIGS. 24, 25, is further arranged to the interface element. It comprises a rod 172 having a generally circular cross-section and is arranged to extend through the central passage 152 of the interface element 150. At the distal end of the activator element 170, a blocking element 174 is attached or made integral with, the activator element 170. The blocking element 174 is generally rectangular and provided with two cut-outs 176 on each side, forming an H-shape when viewed from above as seen in FIG. 25. A distal part 177 of the blocking element 174 is arranged with a material having a certain resiliency when compressed, like foam plastic. The web 178 of the H-shaped blocking element 174 is arranged to fit into a vertical central slit 180 in a plate-shaped post 182, FIG. 26, integrated in the receiving mechanism 126. Further vertical slits 184 are positioned on each side of the central slit 180 in order to create a flexing action in the plane of the post 182. The central slit 180 is further arranged with oppositely directed protrusions 185 that will prevent the arm 164 of the interface element 150 to leave the slit 180 when placed there.

Figure 27:
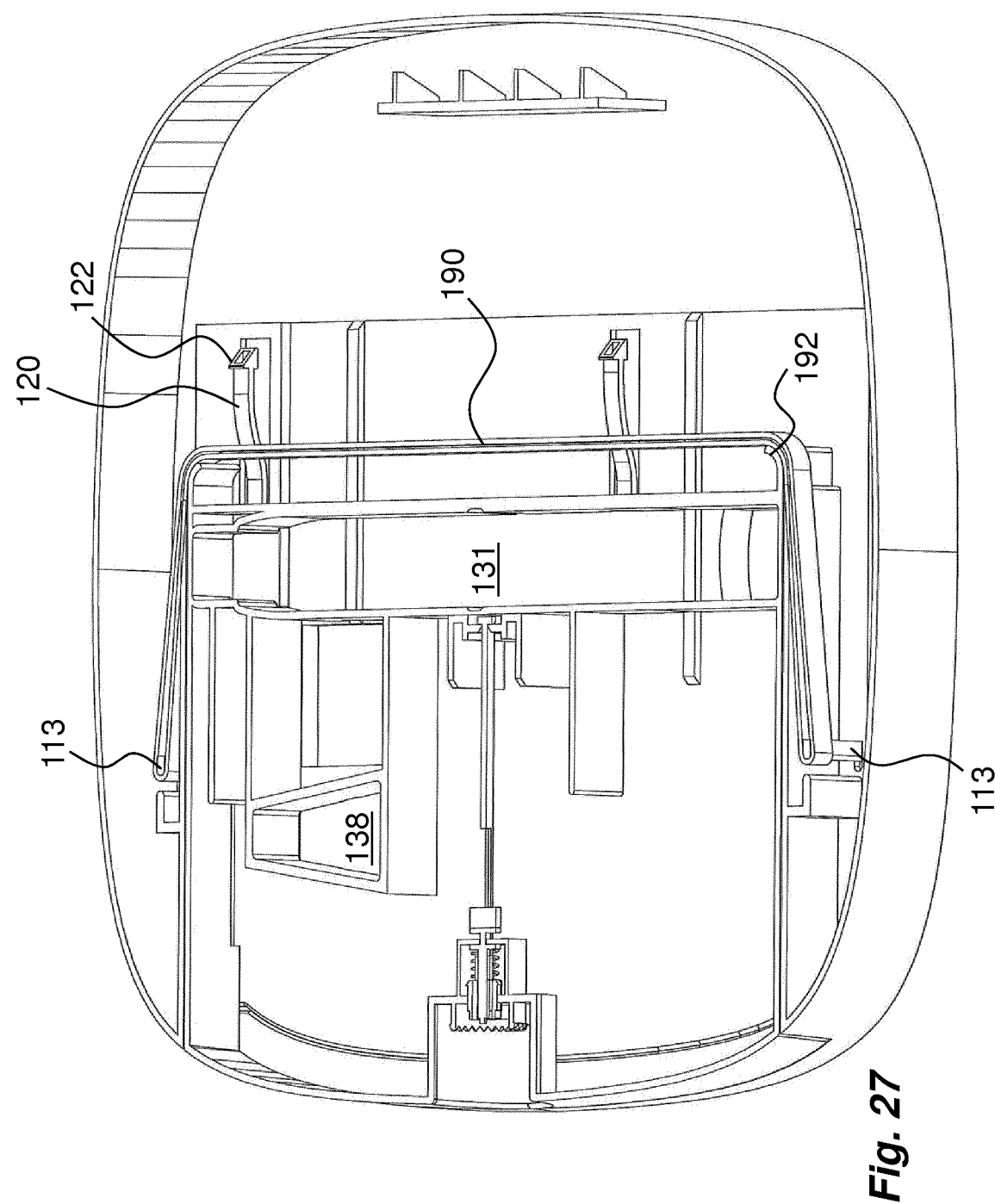

When assembling the unit, the activator element 170 is placed in the central passage 152 of the interface element 150 with the blocking element in the cut-out 168 of the arm 164. When the interface element 150 with the activator element 170 is placed in position in the passage 154 and with the arm 164 in the central slit 180 of the post, the cut-outs 176 of the blocking element 174 will accommodate the plate-shaped post 182. The width of the cut-outs 176 as seen in the longitudinal direction of the activator element 170 is larger than the thickness of the plate-shaped post 182, thereby allowing movement of the activator element 170 in relation to the plate-shaped post 182 as will be described. A spring 186 is further arranged between a distal end surface of the interface element 150 and a proximal surface of the blocking element 174, thereby urging the activator element 170 in the distal direction. The distal end of the arm 164 is further placed in a slit 187 provided in a plate-shaped post 188, FIG. 21, attached to or made integral with the bottom plate 114. Further an elastic member 190, FIG. 27, is arranged with one end around each post 113 of the upper part 102 and runs around support surfaces 192, FIGS. 21, 27, on distal edges of the receiving mechanism, urging it in the proximal direction.

The embodiment shown is intended to function with a monitoring unit developed to be removably attached to the interface of the receiving mechanism. The monitoring unit 200, FIGS. 28-31, comprises a generally tubular housing 202. The monitoring unit 200 has a proximally directed attachment mechanism 204, FIGS. 29 a and b, that is designed to interact with the attachment interface 142. In the embodiment shown, the attachment mechanism 204 comprises a mechanical interface 206 having a central passage which has a shape and dimension so as to fit onto attachment interface 142 of the receiving mechanism.

In order for the connection to be releasable, the attachment end of the monitoring unit 200 is arranged with an attachment mechanism 204 that comprises holding elements in the form of a number of attachment tongues 208, FIG. 29a, that are flexible in the generally radial direction. The free ends of the attachment tongues 208 are arranged with inwardly directed ledges 210 that are to cooperate with the annular ledge 148 of the attachment interface 142. The attachment tongues 208 are attached to a generally tubular body 214, which tubular body 214 is arranged with two oppositely positioned, distally directed, tongues 216. The free ends of the tongues 216 are arranged with cut-outs 218 and proximally directed ledges 220, which ledges are arranged to cooperate with distally directed end surfaces of longitudinally extending ribs 222, on an inner surface of the housing 202. Body 214 is further arranged with a plate-shaped contact element 224 at its proximal end, FIG. 29b, where the contact element 224 is attached to the body 214 by a number of bridges 226. The bridges 226 are placed somewhat radially inwards in relation to the outer surface of the body 214 such that an annular groove 228 is formed.

Further, in the spaces between the bridges 226 the free ends of the attachment tongues 208 are placed. The attachment tongues 208 and the bridges 226 are designed and positioned such that the outer surfaces of the attachment tongues 208 are placed somewhat radially outside the bridges 226. A suitable locking element may be placed in the groove. In one embodiment, the locking element could be a wire spring 230, FIG. 30, that is arranged in the annular groove 228, whereby it is in contact with the outer surface of the attachment tongues 208, providing a resilient force in the outwards radial direction. Of course other types of elements providing resilient forces for removably holding the attachment tongues in engagement with the annular ledge may be employed.

Figure 30:
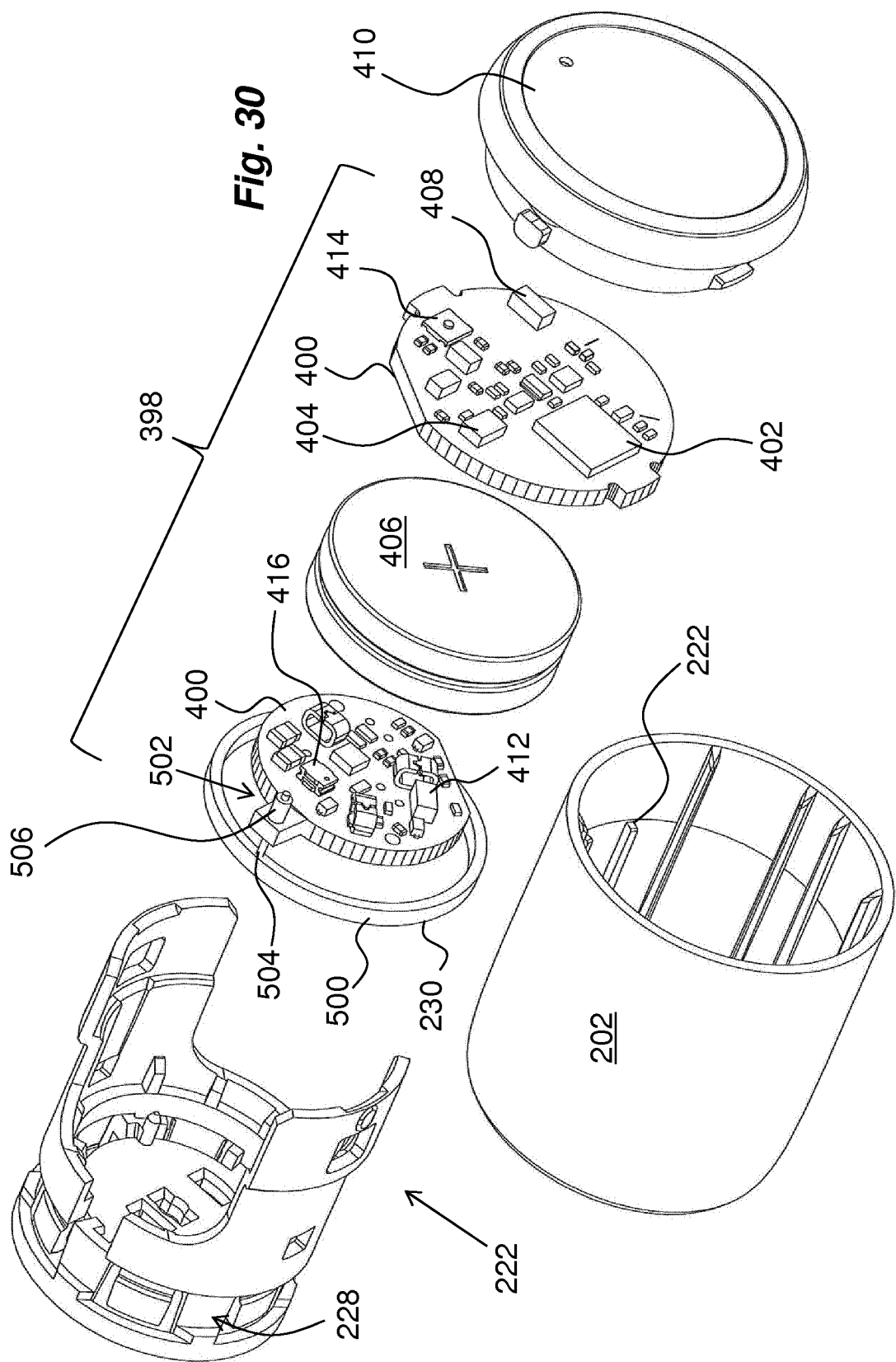

The monitoring unit 200 may optionally be arranged with a more permanent locking mechanism that can be activated when the monitoring unit is attached. It may comprise a locking element 500 that in the embodiment shown in FIGS. 30 and 31 is arranged as a ring 500 which is to be positioned in the groove 228. The width of the ring in the longitudinal direction is smaller than the width of the groove 228. An electronic circuit 400 of the monitoring unit 200 is arranged with a number of drive elements 502, capable of providing linear movement in the longitudinal direction of the monitoring unit 200. The drive elements 502 may for example be linear actuators that often comprise shafts 504 that may be moved linearly in relation to a housing 506. The shaft 504 is connected to the ring 500 so that when the drive element or elements 502 are activated, the ring 500 is moved in the longitudinal direction in the groove.

Figure 28:
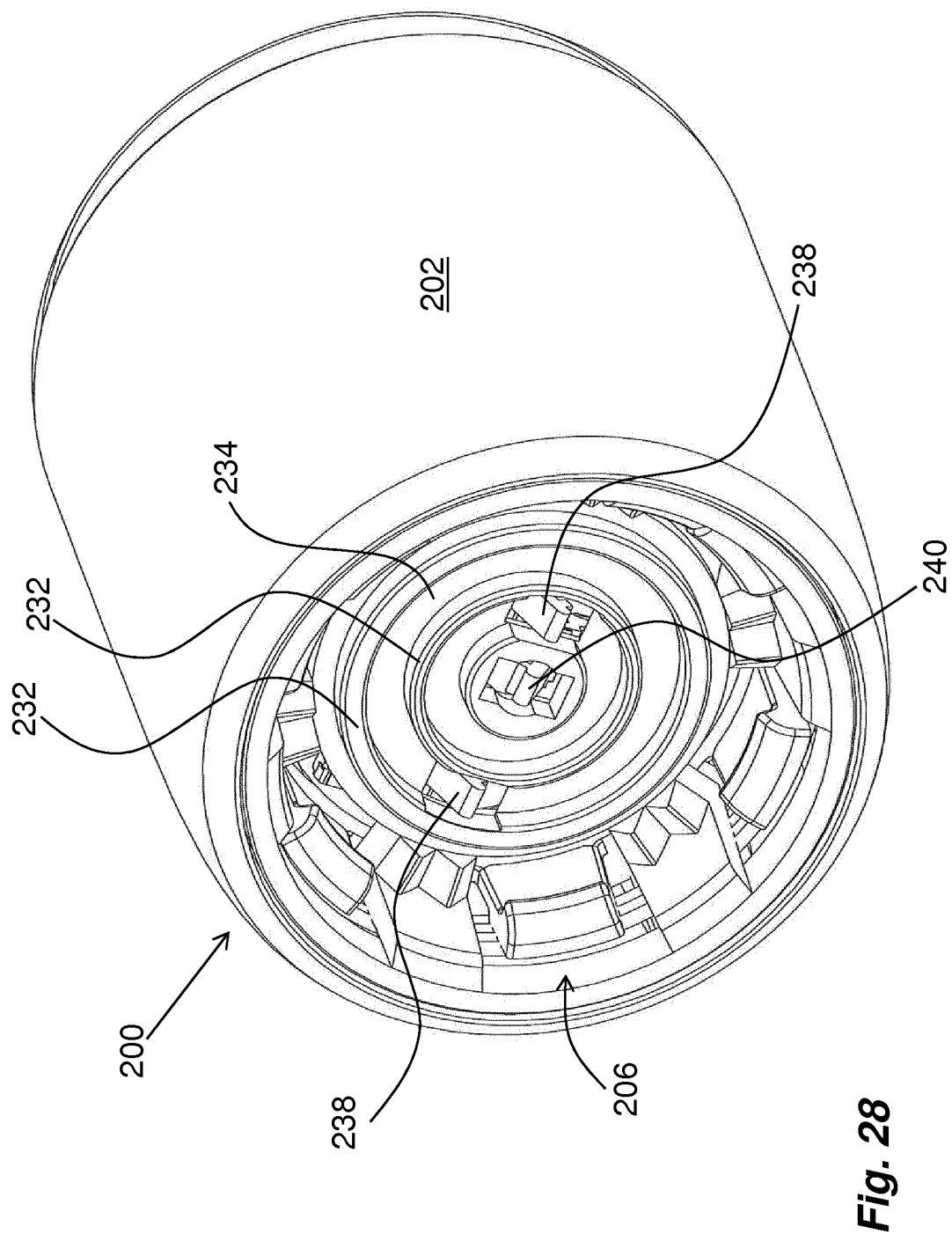
Figure 29:
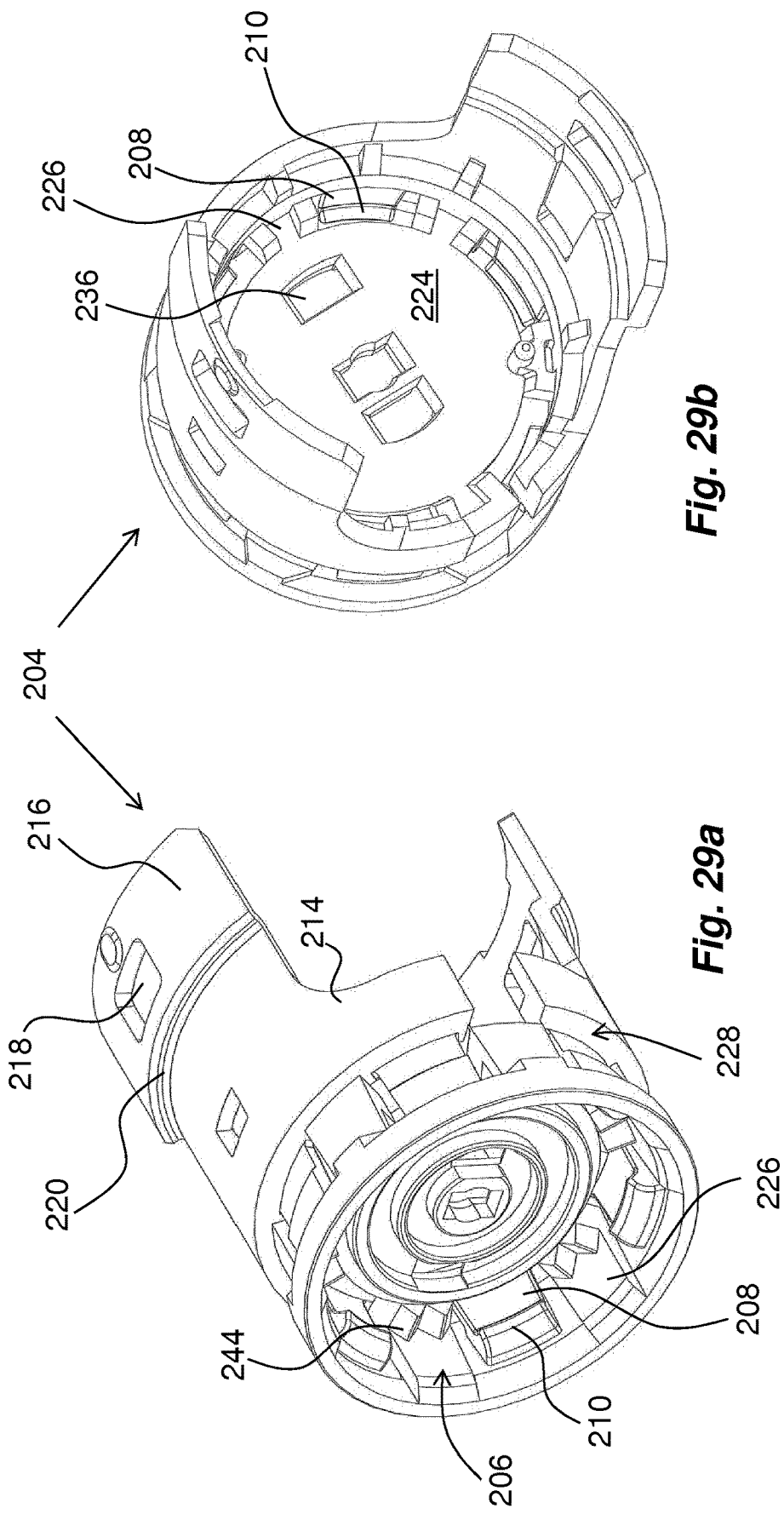

The mechanical interface 206 may comprise a number of rings 232 and grooves 234, FIG. 28, on the proximally directed surface of the contact element 224 having a design that fits together with the proximally directed contact surface of the tubular interface element 150, forming a contact interface. Further, the contact element 224 is preferably arranged with a number of passages 236, FIG. 29b, in which passages 236 switches 238, 240 are placed. The switches are operably connected to electrical switching elements 242, FIG. 31, that will enable activation of the monitoring unit as will be described. Preferably the positions of the switches 238, 240 of the electrical switching elements 242 are arranged in a certain pattern that can be specific for a certain monitoring unit 200 and wherein a certain interface element is arranged with contact surfaces that have the same design so that all switches are activated when the monitoring unit is attached to the attachment interface 142. In this manner, there is a further keying requirement that needs to be fulfilled in order to activate the monitoring unit. For example the contact surfaces are the rings and grooves 232, 234 wherein the switches are positioned at different distances in a radial direction as seen in FIG. 28. The advantage with having rings is that the angular position between the monitoring unit and the receiving mechanism is not important when the two are interconnected. Further, as seen in FIG. 28, since the switches 238, 240 are placed in the grooves 234, manipulation of the switches 238, 240 by fingers is difficult, providing increased security against improper use of the monitoring unit 200.

The interface between the medicament delivery device and the monitoring unit could further comprise mechanical patterns that are to interact with each other. For instance the proximal surface of the contact element 224 could comprise a number of teeth 244, FIG. 29a, for example around a circumference. These teeth 244 are arranged to cooperate with the teeth 146 of the attachment interface 142, the design of the teeth and the positions of the teeth are chosen such that a keying function is obtained. Thus, only monitoring units 200 and receiving mechanisms that have the same pattern can be inter-connected. This provides the possibility of customizing the monitoring unit 200 with the device for handling medical waste products such that only certain connections are possible.

Even though the mechanical interface has been described with annularly arranged teeth and ring-shaped protrusions and ring-shaped grooves, the skilled person can easily design other mechanical configurations that provide a unique keying function.

The monitoring unit 200 is arranged with a number of functions and features that may be activated when the switches 238, 240 are operated, as will be described below, shown in FIGS. 30-31. One basic feature is a monitoring circuit 398 that comprises the electronic circuit 400 that in the embodiment shown is divided onto two generally disk-shaped printed circuit boards. The electronic circuit 400 comprises a processor 402, FIG. 30, capable of processing data program code for performing different tasks. The data program code is preferably stored in appropriate memory elements 404, in which also retrieved data may be stored, as will be described. The monitoring circuit 398 is further arranged with some power supply 406 such as button cells, photovoltaic panels, etc. Further, the above mentioned switches 238, 240 are electronically connected to the electronic circuit 400. In this respect it might be that all switches need to be operated at the same time in order for the monitoring unit to be activated.

The electronic circuit 400 may further be arranged with a user communication circuit 408 that is arranged and programmed to communicate with a user. The user communication circuit 408 may comprise display elements that can communicate visually, e.g. by text stored in the electronic module that is displayed on a suitable display 410 on the monitoring unit, for instance at the distal end where it is clearly visible for a user. In addition to, or instead, the user communication circuit may comprise audio elements 412 that can communicate audibly, e.g. by a recorded message stored in the electronic module that is played in an appropriate loudspeaker of the electronic module or of the device as such.

A further development of the activation function is to provide the monitoring unit 200 with at least one communication circuit 414. The communication technologies that the communication circuit 414 may utilize may comprise near range communication technology such as RFID, NFC or the like, as well as Bluetooth, Ant, ZigBee, just to mention a few. This type of wireless communication technology may also be used to activate the monitoring unit. The communication circuit may be used for monitoring the usage of the device for handling medical waste products such that information is transmitted from the device for handling medical waste products to the monitoring unit 200.

According to a possible feature, if the monitoring unit 200 is provided with communication circuits, then monitored data obtained by the monitoring unit may be transferred to external storage sources and/or external devices. If for instance NFC technology is used, then a mobile NFC-enabled device may derive the monitored data from the usage management module. The same functionality may also be provided when using Bluetooth communication technologies.

The mobile device may then either be capable of processing the data, such as e.g. calculating the time and date of an occurrence of the device for handling medical waste products, such as a time stamp, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the monitoring unit 200 as such. Then the monitoring unit may communicate directly with external data storage sources, data handling centres etc. via the communication networks. The monitored data may preferably be accessible to a physician or the like skilled person that is responsible for the treatment of the user of the medicament delivery device and who might have put together a treatment scheme. This retrieved monitored data may then be evaluated to derive information such as adherence, and the lack of which may lead to measures from the physician.

Figure 15:
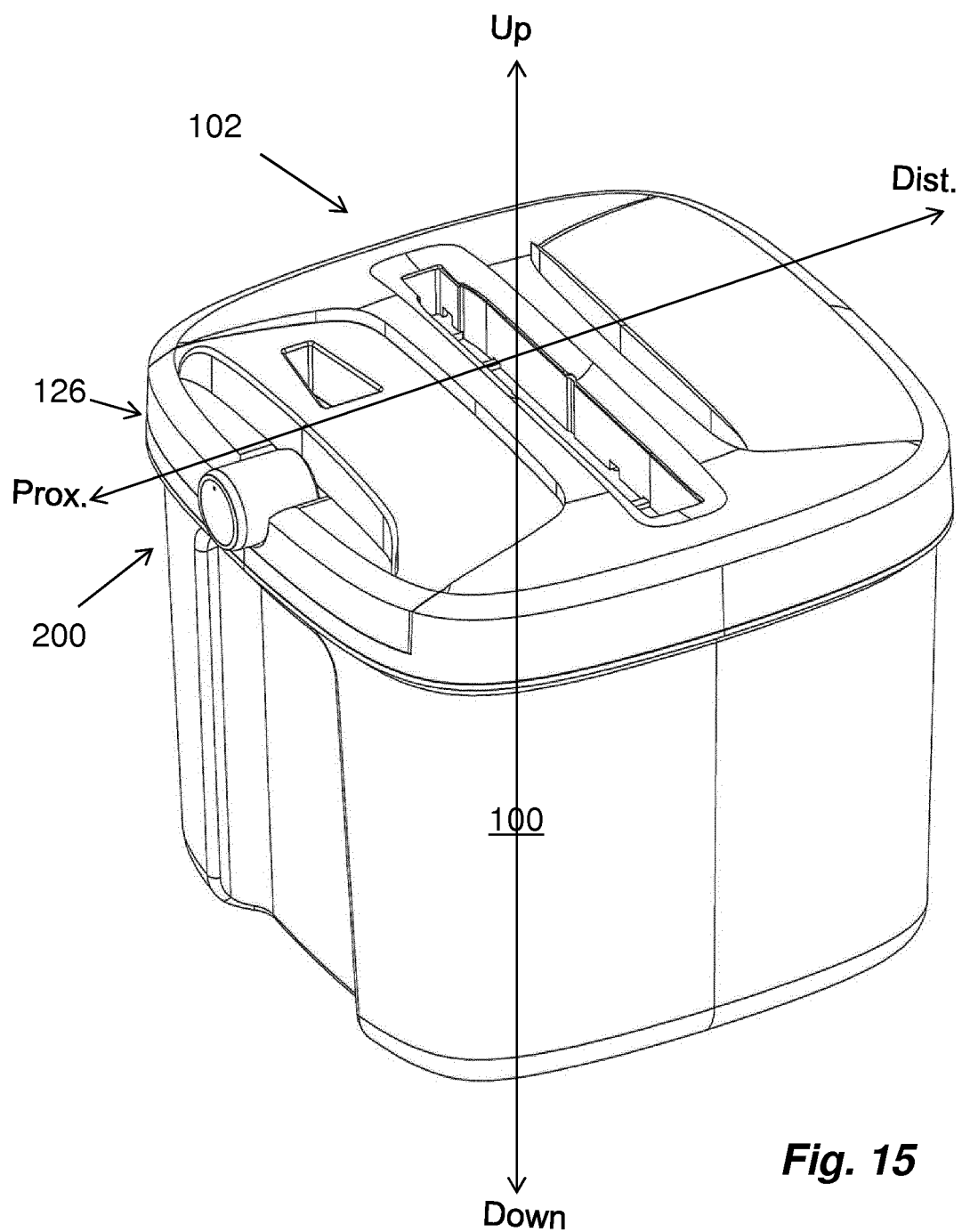
FIG. 15 shows a perspective view of another embodiment of the device.
Figure 16:
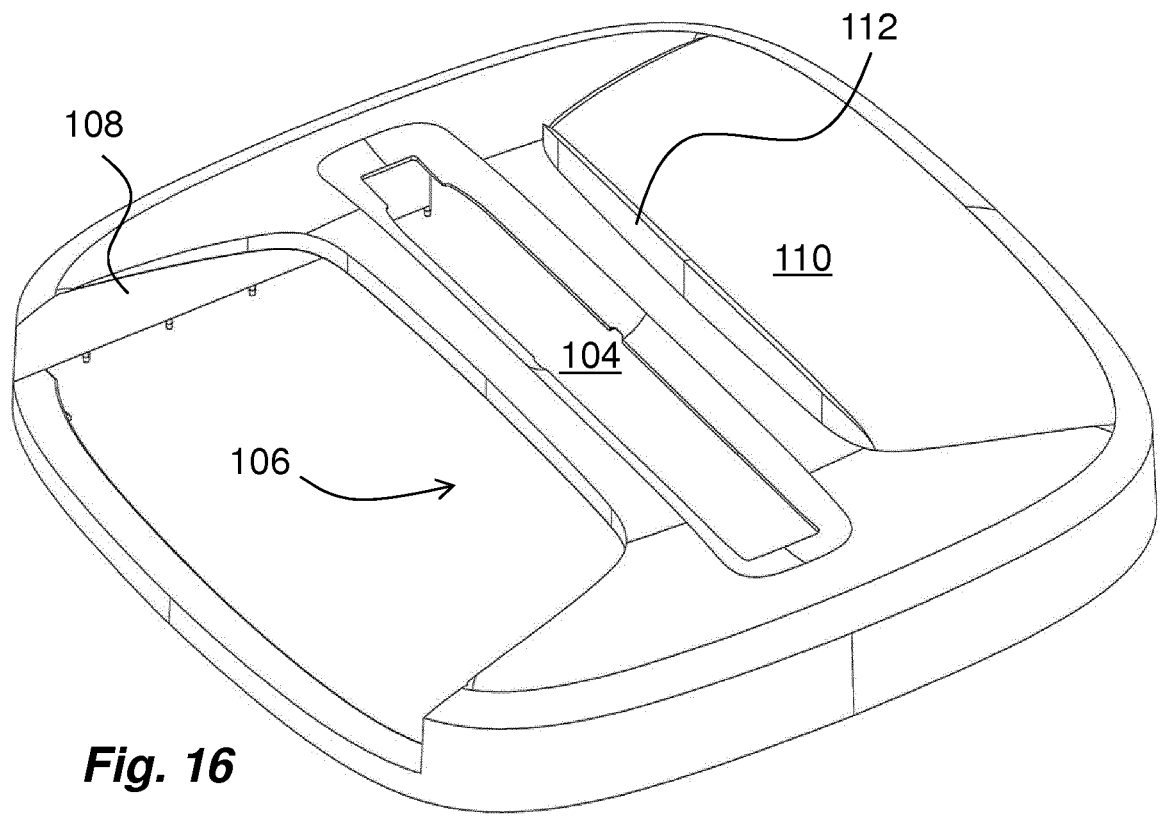
Figure 32:
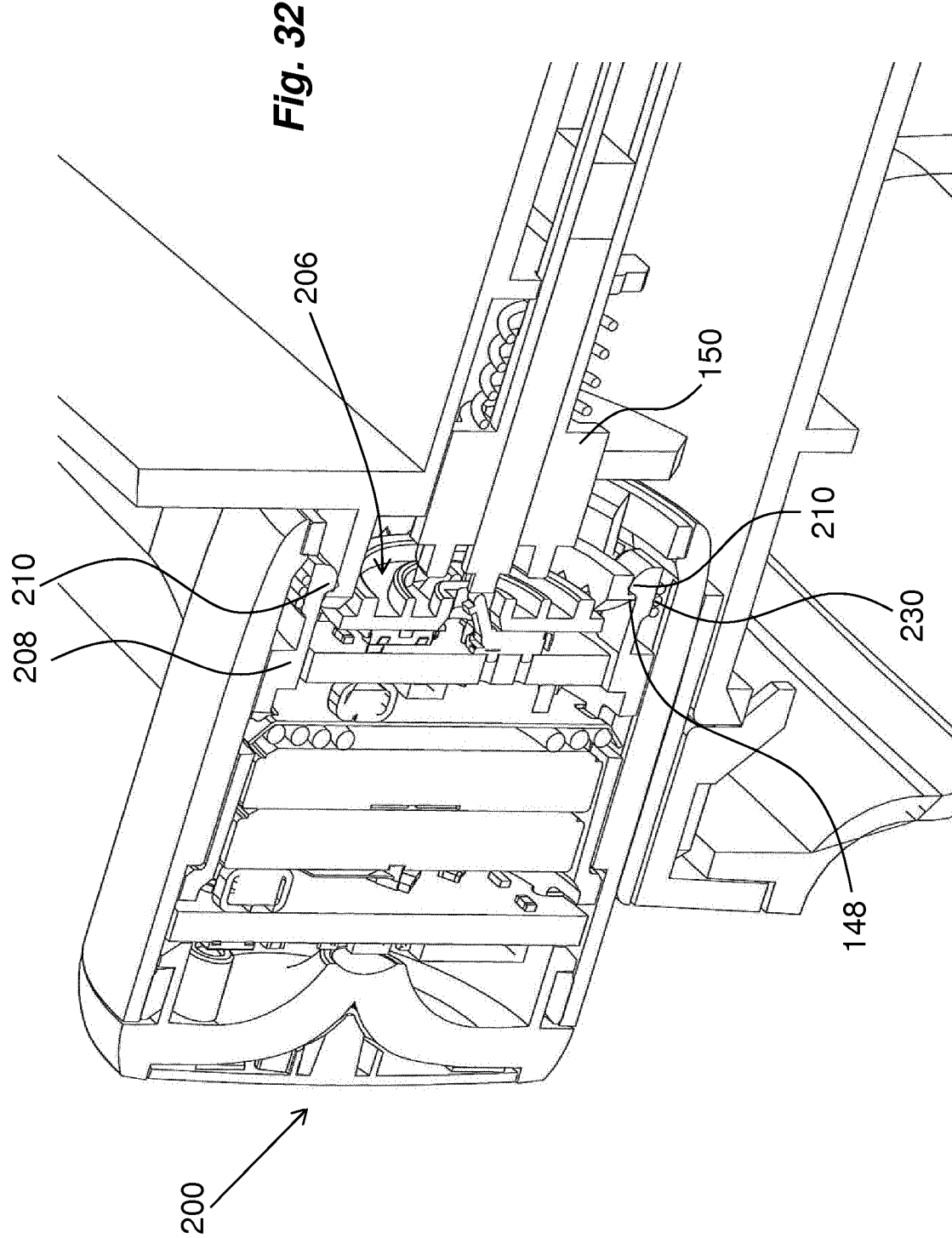

The device is intended to function as follows. When not in use, the receiving mechanism 126 is in its most proximal position by the elastic member 190, which position is shown in FIG. 15. In this position, the first compartment 131 is placed under the first passage 104 as seen in FIG. 15. When a used medicament delivery device is to be discarded, the medical waste device is made ready to obtain information by attaching a monitoring unit 200. The flexible tongues 208 with their ledges 210 will then interact with the annular ledge 148 of the attachment interface 142 so that the monitoring unit 200 is detachably attached to the receiving mechanism as seen in FIG. 32. The wire spring 230 apply a force in the radial inwardly direction for maintaining the attachment. The pattern of teeth 244 of the monitoring unit 200 is designed to interconnect with the pattern of teeth 146 of the attachment interface 142 of the receiving mechanism 126. In this initial, attached, position there is preferably a distance between the proximal end of the interface element 150 and the interface 206 of the monitoring unit as well as a distance between the proximal end of the activator element 170 and the interface of the monitoring unit, as seen in FIG. 32, wherein the switches 238, 240 of the monitoring unit 200 are non-activated such that the monitoring unit is sleeping. This feature may be for saving power of the power source of the monitoring unit, because a user may attach the monitoring unit and then leave it like that for many hours until the device is actually used for discarding a medicament delivery device.

Figure 33:
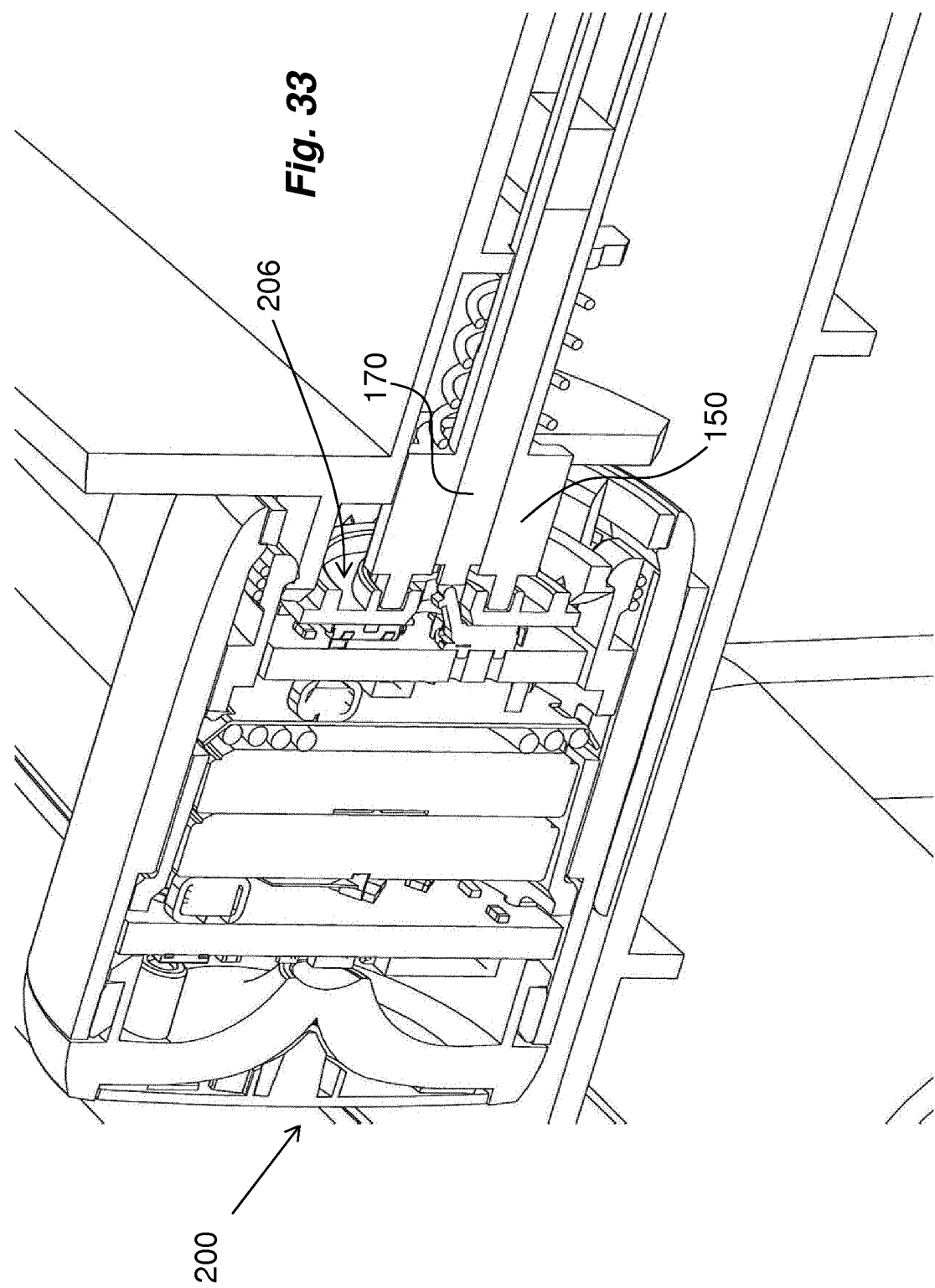

A used medicament delivery device may now be placed in the first passage 104, whereby it enters the first compartment 131 of the receiving mechanism 126. If the medicament delivery device has been arranged with a medicament delivery member shield remover, this may be placed in the second compartment 138 of the receiving mechanism 126. The user now pushes the receiving mechanism 126 into the upper part 102 by using its fingers to grip the vertical ledges 112, 140 of the upper part 102 and the receiving mechanism 126 and press them towards each other, wherein the movement of the receiving mechanism 126 is guided by the guide ledges 124 on the bottom plate 114 cooperating with the first cut-outs 134 of the receiving mechanism 126. The pushing action will cause the proximal end surface of the interface element 150 to come in contact with activation switches 238 in that its circular end surface will fit between the rings 232 of the mechanical interface 206 of the monitoring unit as seen in FIG. 33. However, the activator element 170 is not yet in contact with the mechanical interface 206 of the monitoring unit.

The contact with the activation switches will "wake up" or activate the monitoring unit to make it ready for obtaining and transmitting information. The waking up may be communicated to a user in an appropriate way, informing the user that the monitoring unit is ready to be used. The information may be presented visually or audially by the user communication circuit 408. When the receiving mechanism is pushed further into the upper part, the arms 120 of the bottom plate 114 will come in contact with the second cut-outs 136 of the receiving mechanism 126.

Figure 34:
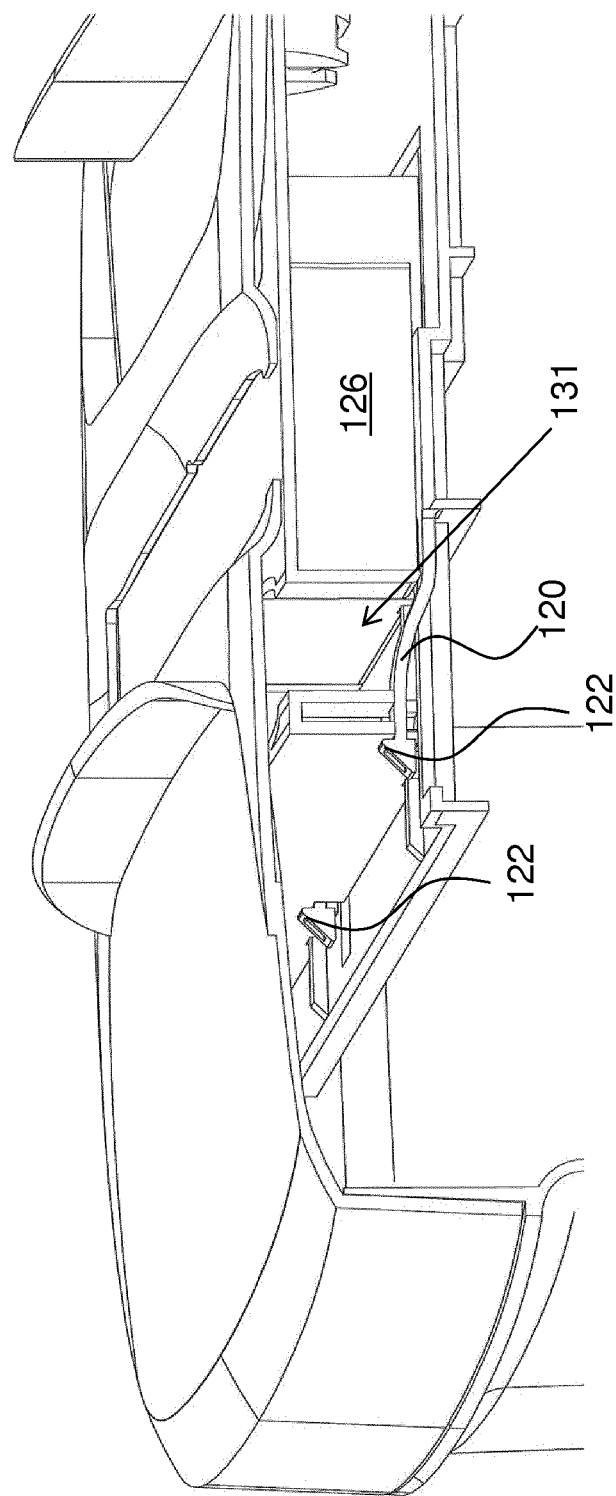
FIGS. 34-38 show cross-sectional views of the device of FIG. 15 in different functional states.
Figure 35:
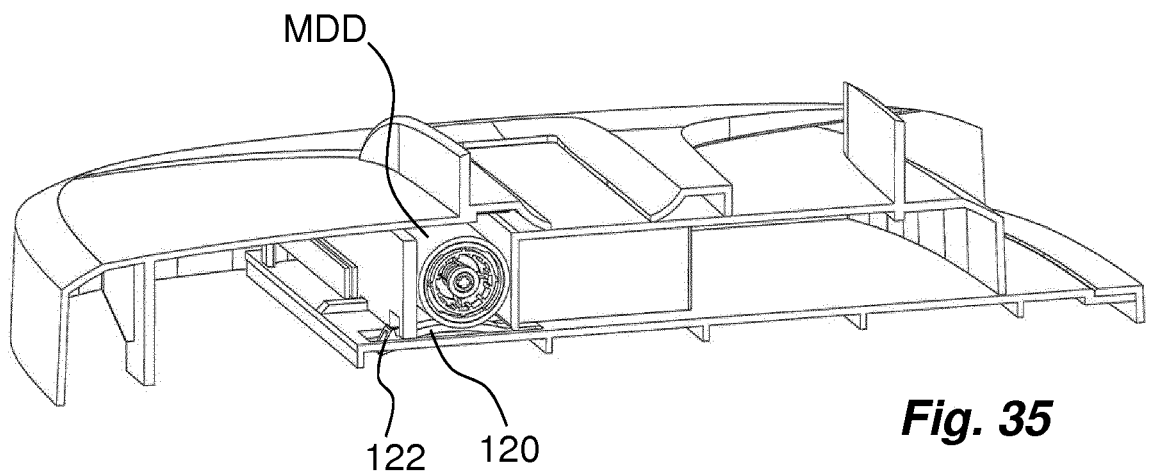

If no medicament delivery device was present in the first compartment 131, then the upwardly directed hooks 122 would engage the distal surface of the compartment, preventing any further movement of the receiving mechanism as shown in FIG. 34. When a medicament delivery device, MDD, is placed in the first compartment 131, its shape is arranged to have a keying function in that the housing of the medicament delivery device will come in contact with the contact surfaces 119 of the arms 120 of the bottom plate 114 and press the arms 120 downwards so that the hooks 122 will not engage with the distal wall of the compartment as seen in FIG. 35.

If the medicament device has been used for delivering medicament, there may be parts of the medicament delivery device that have changed position, e.g. protrude out of the housing of the medicament delivery device. For example, a medicament delivery device may comprise a medicament delivery member guard that after use extends or protrudes in order to cover or guard the medicament delivery member which is an important feature if the medicament delivery member for example is an injection needle. If so, this may be used for allowing only used medicament delivery devices to be discarded and preventing unused medicament delivery devices from being discarded.

Figure 36:
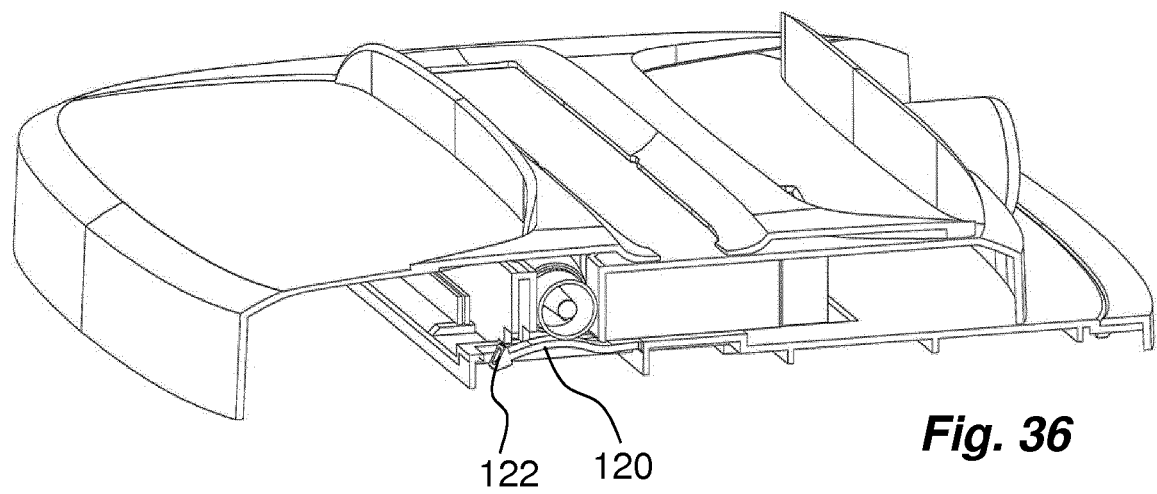

According to one feasible solution, the medicament delivery member guard is used as a keying element for allowing the disposal into the device for handling medical waste products. As seen in FIG. 36, when the receiving mechanism 126 with the medicament delivery device MDD is moved distally, the medicament delivery member guard will come in contact with the arms 120 of the locking mechanism wherein the arms are pressed downwards so that the first compartment 131 containing the medicament delivery device can pass the hooks 122. In this position the top area 110 acts as a blocking element, preventing access to the compartment 131.

Figure 37:
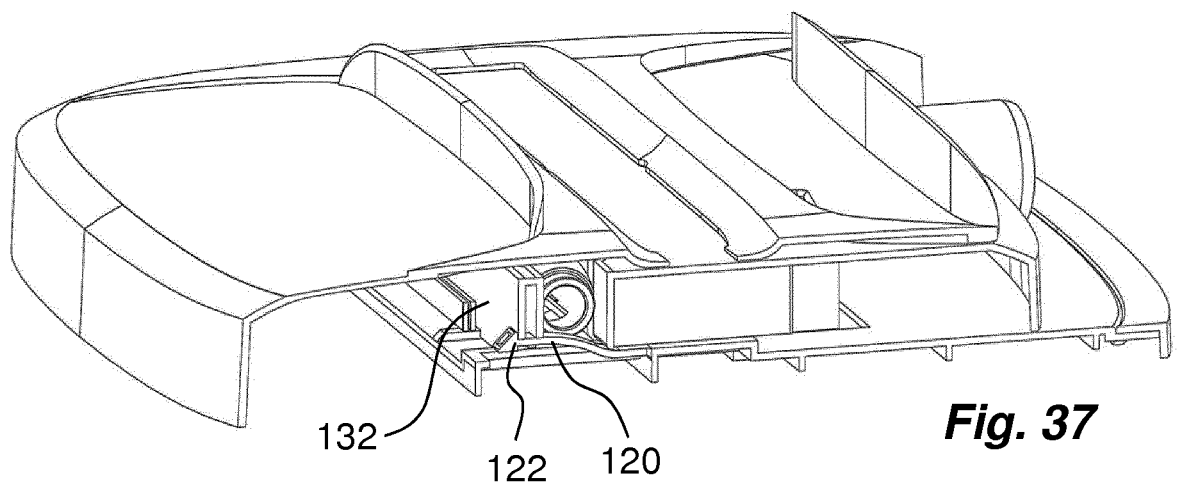
Figure 38:
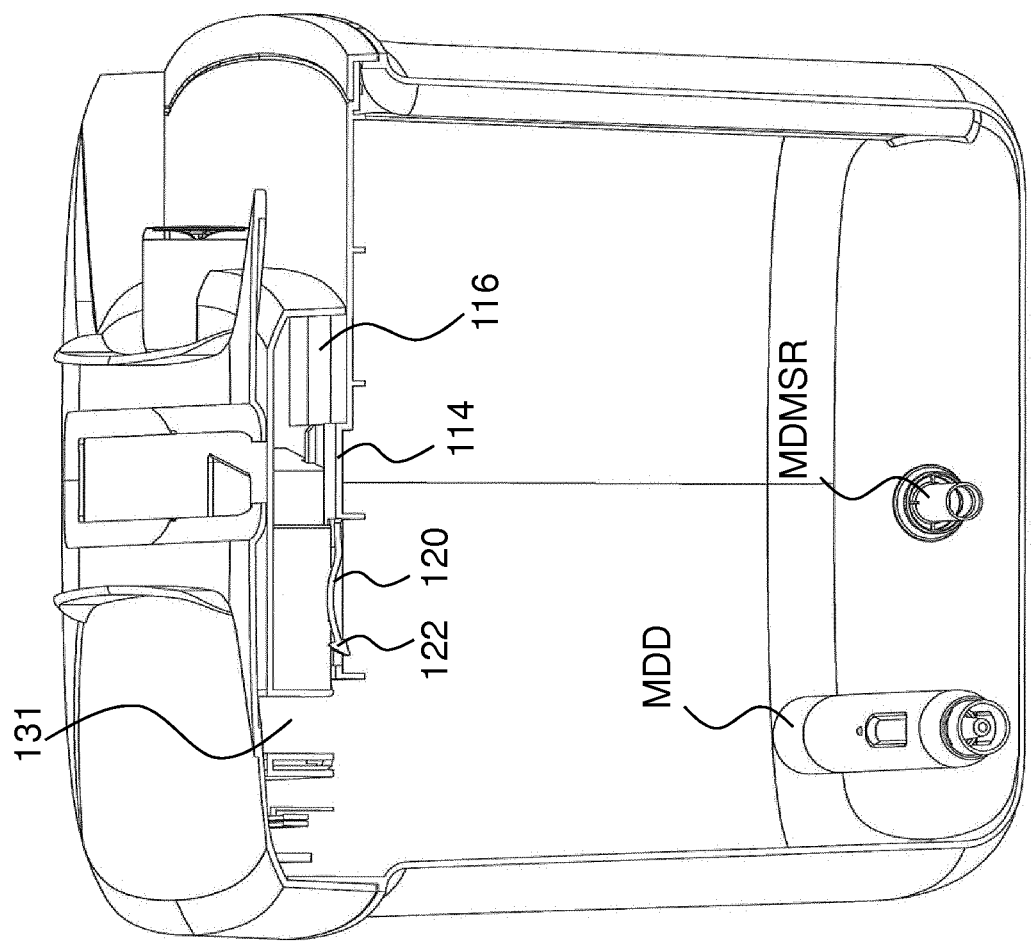
Figure 39:
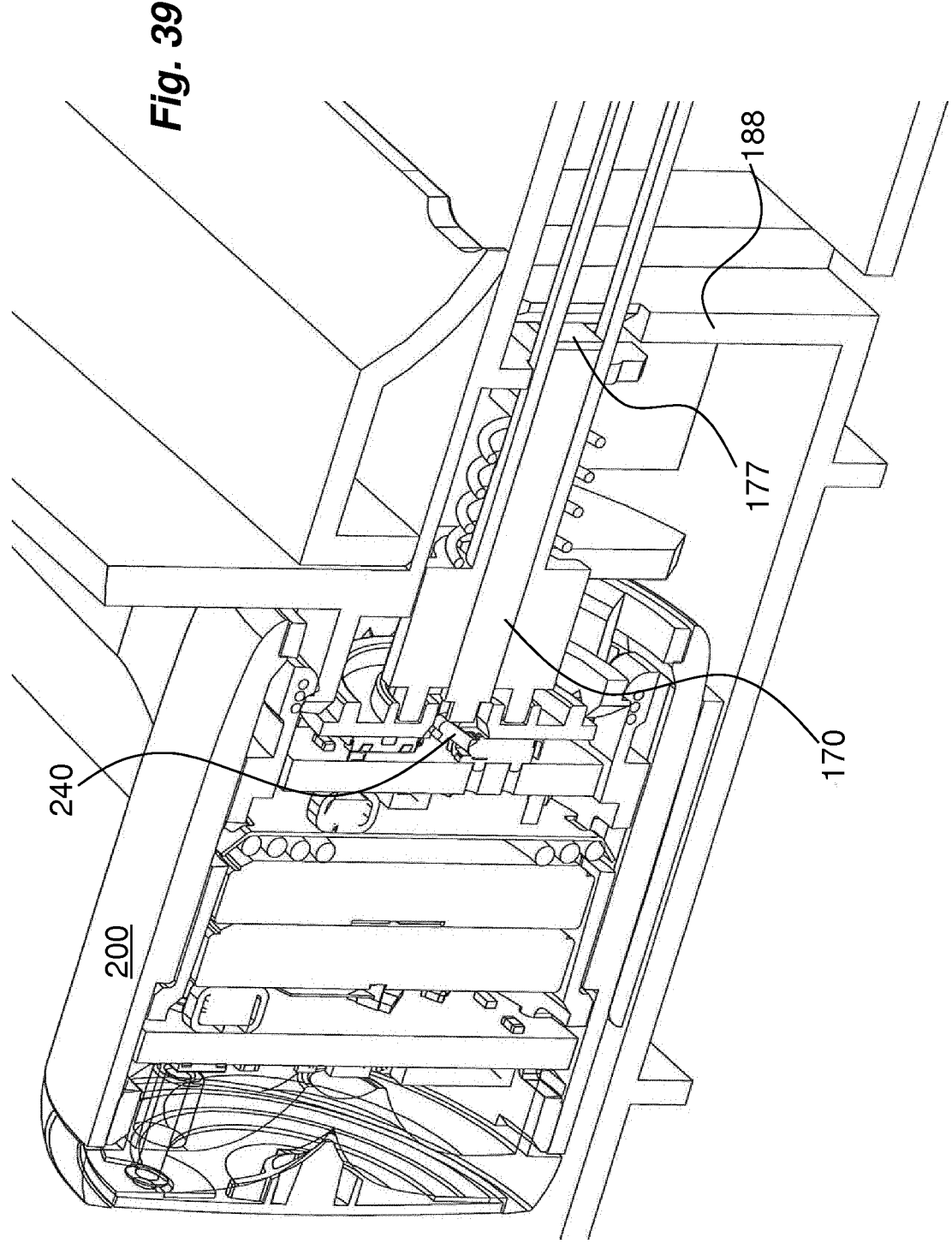

However, if the medicament delivery device MDD that is put in the compartment is unused, FIG. 37, the medicament delivery member guard is not protruding at the proximal end of the medicament delivery device and the arm 120 adjacent the proximal end of the MDD will not be pressed down but will fit into the second cut-out 136 at the vertical wall 132 of the compartment, wherein the upwardly directed hook 122 of the arm 120 will engage with the vertical wall 132 and lock the receiving mechanism 126 from moving further. The unused medicament delivery device can thus not be discarded in the waste receptacle.

On the other hand, if a used medicament delivery device has been entered into the first compartment 131 it will press down both arms 120 of the bottom plate 114 so that the first compartment 131 may pass the hooks 122 of the arms 120. The first compartment then slides past the distal edge of the bottom plate 114, whereby the medicament delivery device MDD will fall into the waste bin, FIG. 38. Further, if the medicament delivery device is arranged with a medicament delivery member shield remover MDMSR, that may be placed in the second compartment 138 and when the receiving mechanism 126 is pushed in the distal direction, the second compartment 138 will pass the passage 116 in the bottom plate 114, whereby the medicament delivery member shield remover MDMSR will fall into the waste receptacle, FIG. 38. At the end of the movement of the receiving mechanism 126 for disposing a used medicament delivery device, the distal part 177 with resilient material of the blocking element 174 comes in contact with the proximally directed surface of the plate-shaped post 188 of the bottom plate 114 and is compressed, FIG. 39. This causes the activator element 170 to come to a stop, whereby its proximal end will protrude out of the attachment interface 142 of the receiving mechanism 126 and press on the centrally positioned switch 240 of the monitoring unit 200. This will trigger the electronics to register that a medicament delivery device has been discarded. This information may then be handled in many ways as described above.

Even though the receiving mechanism has been described with a sliding movement from the first position to the second position, it is to be understood that there also could be a turning/pivoting movement of the compartment from the first position to the second position, wherein the locking mechanism will lock the compartment from being turned until a specific medicament delivery device has been placed in the compartment. Further, the detection mechanism has been described above with a mechanical contact element, but it is to be understood that other technologies may be used such as e.g. a light beam that is broken by the receiving mechanism, which is detected; a magnetic, capacitive, resistive element attached to or embedded in the receiving mechanism that is moved in the vicinity of a sensor in the monitoring unit capable of detecting the presence of the element, just to mention a few possible solutions.

It is to be understood that the embodiments described above and shown in the drawings are to be regarded only as non-limiting examples and that the invention may be modified in many ways within the scope of the patent claims.

The invention claimed is:

1. A device for receiving and handling specific medical waste products to be stored in a safe container, comprising a receiving mechanism arranged with:
   a compartment for receiving a medicament container,
   wherein the compartment is operably arranged to be moved from (i) a first position in which a medical waste product may be entered into said compartment to (ii) a second position in which the medical waste product is entered into the safe container,
   at least one first locking element operably arranged to releasably lock said compartment from being moved from said second position,
   said at least one first locking element comprising at least one contact surface, wherein the at least one contact surface is arranged to be engaged by an outer surface of a medical waste product placed in the compartment, which unlocks the compartment so that the compartment can be moved to said second position, and
   a monitoring unit comprising a detection mechanism configured to detect that said compartment has been moved from said first position to said second position.

2. The device according to claim 1, wherein said compartment has a form generally corresponding to a shape of the specific medical waste product to be stored in the safe container.

3. The device according to claim 1, wherein said at least one first locking element comprises at least one flexible arm, and wherein the at least one flexible arm comprises said at least one contact surface.

4. The device according to claim 3, wherein said at least one flexible arm further comprises a stop ledge arranged to act on said compartment for providing a lock against movement of said compartment.

5. The device according to claim 1, further comprising a blocking element arranged to block access to said compartment when said compartment is in the second position.

6. The device according to claim 1, wherein said receiving mechanism is configured to provide one or more of a linear motion of said compartment from said first position to said second position or a rotary motion of said compartment from said first position to said second position.

7. The device according to claim 1, wherein said monitoring unit is releasably attached to the device.

8. The device according to claim 7, further comprising a second locking element operably arranged to lock said compartment in said first position when said monitoring unit is not attached to the device.

9. The device according to claim 1, wherein said monitoring unit comprises an electronic circuit that is configured to provide a triggering signal each time said detection mechanism is operated.

10. The device according to claim 9, wherein said electronic circuit is configured to provide a time stamp by the triggering signal each time said detection mechanism is operated.

11. The device according to claim 10, wherein said electronic circuit further comprises storage means that is configured to store said time stamps.

12. The device according to claim 10, further comprising a communication unit, operably arranged to communicate said triggering signals or said time stamps to one or more external information receivers.

13. The device according to claim 12, wherein said communication unit comprises a wireless communication circuit, and wherein said wireless communication circuit is configured to communicate via at least one of a near range communication technology, a cellular radio communication network or a local area network.

14. The device according to claim 9, wherein said electronic circuit further comprises one or more user alert elements, wherein said electronic circuit is arranged to active said one or more user alert elements at certain time intervals and wherein said one or more user alert elements comprise at least one of a visual element, an audible element, or a tactile element.

15. The device according to claim 1, further comprising a mechanical interface arranged to interact with a mating mechanical interface arranged on said monitoring unit, and an activation switch arranged to activate said monitoring unit.

16. The device according to claim 15, wherein said mechanical interface further comprises a plurality of mechanical keying elements arranged with specific mechanical keying design and wherein said mating mechanical interface of said monitoring unit is arranged with a plurality of keying elements with a mating specific keying design.

17. The device according to claim 16, wherein said plurality of mechanical keying elements comprise a plurality of protrusions and a plurality of recesses arranged in one or more predetermined patterns.

18. The device according to claim 17, wherein said activation switch is positioned in said mechanical interface such that said activation switch is activated mechanically by said plurality of protrusions.

19. The device according to claim 16, wherein said plurality of mechanical keying elements comprise teeth.

* * * * *